US007652050B2

(12) United States Patent
Sandino et al.

(10) Patent No.: US 7,652,050 B2
(45) Date of Patent: Jan. 26, 2010

(54) METHODS FOR INCREASING THE SURVIVAL OF AQUATIC ANIMALS INFECTED WITH AN AQUATIC VIRUS

(75) Inventors: Ana Maria Sandino, Santiago (CL); Geraldine Z. Mlynarz, Santiago (CL)

(73) Assignee: Laboratorio de Siagnóstico GAM S.A, Santiago (CL)

( * ) Notice: Subject to any disclaimer, the term of this patent is extended or adjusted under 35 U.S.C. 154(b) by 670 days.

(21) Appl. No.: 10/314,366

(22) Filed: Dec. 9, 2002

(65) Prior Publication Data

US 2003/0191169 A1 Oct. 9, 2003

Related U.S. Application Data

(60) Provisional application No. 60/336,684, filed on Dec. 7, 2001.

(51) Int. Cl.
*A61K 31/42* (2006.01)
(52) U.S. Cl. .................................................. 514/378
(58) Field of Classification Search ................ 514/372, 514/378
See application file for complete search history.

(56) References Cited

U.S. PATENT DOCUMENTS

| | | | |
|---|---|---|---|
| 3,878,047 A | 4/1975 | Hanka et al. | |
| 4,188,324 A | 2/1980 | Martin | |
| 4,225,720 A | 9/1980 | Martin | |
| 4,232,164 A | 11/1980 | Martin | |
| 4,256,898 A | 3/1981 | Kelly et al. | |
| RE31,578 E | 5/1984 | Kelly et al. | |
| 4,843,087 A | 6/1989 | Diana | |
| 4,892,882 A * | 1/1990 | Tomita et al. ................ | 514/380 |
| 5,087,639 A * | 2/1992 | McGovren et al. ........... | 514/561 |
| 5,371,085 A | 12/1994 | Nakano et al. | |
| 5,464,848 A | 11/1995 | Diana et al. | |
| 5,643,929 A | 7/1997 | Diana et al. | |

OTHER PUBLICATIONS

Keast et al, 117CA:103654, 1992.*
Hanka et al, 79CA:100631, 1984.*
Martin et al, 82CA:132911, 1984.*
Dobos et al. 1980CA:18696.*
Keast et al. (Inhibition in vitro of the replication of murine cytomegalovirus or reovirus type 3 by the glutamine analogue acivicin, Arch Virol (1992) 124, pp. 235-249)3.*
Dobos (Protein-Primed RNA Synthesis in vitro by the Virion-Associated RNA Polymerase of Infectious Pancreatic Necrosis Virus, Virology (1995) 208, pp. 19-25).*
Hudson et al. (The efficacy of amantadine and other antiviral compounds against two salmonid viruses in vitro, Antiviral Research, 1988, vol. 9, pp. 379-385).*
Dobos, P., "Protein-Primed RNA Synthesis in Vitro by the Virion-Associated RNA Polymerase of Infectious Pancreatic Necrosis Virus," Virology 208, 19-25 (1995).
Dobos, P., "In Vitro Guanylylation of Infectious Pancreatic Necrosis Virus Polypeptide VP1," Virology 193,403-413 (1993).
Hudson, J.B., Graham, E.A. and Simpson, M.F., "The efficacy of amantadine and other antiviral compounds against two salmonid viruses in vitro," Antiviral Research 9, 379-385 (1988).
Jashés, M. González, M., López-Lastra, M., De Clercq, E. and Sandino, A., "Inhibitors of infectious pancreatic necrosis virus (IPNV) replication," Antiviral Research 29, 309-312 (1996).
Jashés, M., Mlynarz, G., De Clercq, E. and Sandino, A.M., "Inhibitory effects of EICAR on infectious pancreatic necrosis virus replication," Antiviral Research 45, 9-17 (2000).
Keast, D. and Vasquez, A.R., "Inhibition in vitro of the replication of murine cytomegalovirus or reovirus type 3 by the glutamine analogue acivicin," Archives of Virology 124: 235-244 (1992).
Migus, D.O. and Dobos, P., "Effect of Ribavirin on the Replication of Infectious Pancreatic Necrosis Virus in Fish Cell Cultures," Journal of General Virology 47, 47-57 (1980).
Moya, J., Pizarro, H., Jashés, M., De Clercq, E. and Sandino, A.M., "In vivo effect of EICAR (5-ethynly-1-β-D-ribofuranosylimidazole-carboxamide) on experimental infected rainbow trout (*Oncorhynchus mykiss*) and coho salmon (*Oncorhynchus kisutch*) fry with infectious pancreatic necrosis virus," Antiviral Research 48, 125-130 (2000).
Savan, M. and Dobos, P., "Effect of virazole on rainbow trout *Salmo gairdneri* Richardson fry infected with infectious pancreatic necrosis virus," Journal of Fish Diseases 3, 437-440 (1980).
Woods, M.G., Diana, G.D., Rogge, M.C., Otto, M.J., Dutko, F.J. and McKinlay, M.A., "In vitro and in vivo activities of WIN 54954, a new broad-spectrum antipicornavirus drug" (abstract), Antimicrob. Agents Chemother. 33(12): 2069-74 (Dec. 1989).
Crane, M.S., Hardy-Smith, P., Williams, L.M., Hyatt, A.D., Eaton, L.M., Gould, A., Handlinger, J., Kattenbelt, J. and Gudkovs, N., "First isolation of an aquatic birnavirus from farmed and wild fish species in Australia" (abstract) Dis. Aquat. Organ. 43(1), 1-14 (Oct. 25, 2000).
Blake, S., Ma, J.Y., Caporale, D.A., Jairath, S. and Nicholson, B.L., "Phylogenetic relationships of aquatic birnaviruses based on deduced amino acid sequences of genome segment A cDNA" (abstract) Dis. Aquat. Organ. 45(2), 89-102 (Jun. 2001).

(Continued)

*Primary Examiner*—Sreeni Padmanabhan
*Assistant Examiner*—Sahar Javanmard
(74) *Attorney, Agent, or Firm*—Merchant & Gould P.C.

(57) ABSTRACT

A method of increasing the survival of animals and aquatic species susceptible to birnavirus infection by treating them before, during and/or after birnavirus exposure, with a chemical compound capable of inhibiting viral replication. A method of treating aquatic species to increase their survival in the presence of a virus, particularly an aquatic birnavirus, and to increase the yield of farmed fish susceptible to viral infection. The present invention provides methods for increasing survival of virally-exposed aquatic animals by administering therapeutically effective amounts of isoxazol compounds to aquatic animals susceptible to birnavirus infection and/or IPNV infection, particularly in fish such as salmonoid species, which are easily exposed to IPNV. The present invention also provides methods for increasing survival of virally-exposed animals by administering therapeutically effective amounts of isoxazol compounds to farmed animals susceptible to birnavirus infection and/or IBDV infection, particularly in poultry such as chickens, which are exposed to IBDV.

23 Claims, 10 Drawing Sheets

OTHER PUBLICATIONS

Blake, S.L., Schill, W.B., McAllister, P.E., Lee, M.K., Singer, J.T. and Nicholson, B.L., "Detection and identification of aquatic birnaviruses by PCR assay" (abstract), Journal of Clinical Microbiology 33(4), 835-9 (Apr. 1995).

Balzarini, J., Stet, L., Matsuda, A., Wiebe, L., Knauss, E. and De Clercq, E., "Metabolism of EICAR (5-ethynyl-1-beta-D-ribofuranosylimidazole-4-carboxamide), a potent inhibitor of inosinate dehydrogenase" (abstract) Adv. Exp. Med. Biol. 431, 723-8 (1998).

Kitaoka, S. Konno, T. and De Clercq, E., "Comparative efficacy of broad-spectrum antiviral agents as inhibitors of rotavirus replication in vitro" (abstract) Antiviral Res. 6(1), 57-65 (Jan. 1986).

Novoa, B., Blake, S., Nicholson, B.L. and Figueras, A., "Comparison of different procedures for serotyping aquatic birnavirus" (abstract) Appl. Environ. Microbiol. 61(8), 2925-9 (Aug. 1995).

Vaidehi, N. and Goddard, W.A., "The pentamer channel stiffening model for drug action on human rhinovirus HRV-1A," Proc. Natl. Acad. Sci. USA, vol. 94, 2466-2471 (Mar. 1997).

Wang, W., Lee, W.M., Mosser, A.G. and Rueckert, R.R., "WIN 52035-Dependent Human Rhinovirus 16: Assembly Deficiency Caused by Mutations near the Canyon Surface," Journal of Virology 72(2), 1210-1218 (Feb. 1998).

McAllister E., "Infecciones viricas de peces cultivados: Birnavirus de peces," in In Patología en Acuicultura, ed. by Espinosa de los Monteros, J. et al. Industrias Gráficas España, S.L., Ch. 2 at Table IV (1988).

European Search Report dated Oct. 20, 2005.

Hasobe et al.; "Antiviral Activity and Its Mechanism of Guanine 7-N-Oxide on DNA and RNA Viruses Derived From Salmonid"; The Journal of Antibiotics; Jul. 18, 1985; vol. 38 No. 11; Japan; pp. 1581-1587.

"Acivicin Antineoplastic" Drugs Fo the Future, Barcelona, ES. vol. 18, No. 4, 1993, p. 362.

Gil-Fernandez et al.; "Comparative Efficacy of Broad-Spectrum Antiviral Agents as Inhibitors of African Swine Fever Virus Replication in Vitro"; Sep. 26, 1986; pp. 151-160; Elsevier Science Publishers B.V. (Biomedical Division).

Smee et al; "Inhibition of Rotaviruses by Selected Antiviral Substances: Mechanisms of Viral Inhibition and in Vivo Activity"; Oct. 1, 1981; pp. 66-73; vol. 21, No. 1; Utah.

Bashai, "The in vivo-in vitro paradox in pneumococcal respiratory tract infections." Journal of Antimicrobial Chemotherapy, vol. 49, pp. 433-436 (2002).

Clercq, et al., "Broad-Spectrum Antiviral Activities of Neplanocin A, 3-Deazaneplanocin A, and Their 5'-Nor Dervaitives." Antimicrobial Agents and Chemotherapy, vol. 33, No. 8, pp. 1291-1297 (1989).

Dargan, et al., "The effect of cicloxolone sodium on the replication in cultured cells of adenovirus type 5, reovirus type 3, poliovirus type 1, two bunyaviruses and Semliki Forest Virus." Journal of General Virology, vol. 73, pp. 407-411 (1992).

Fernandez-Larrson and Patterson, "Ribavirin is an Inhibitor of Human Immunodeficiency Virus Reverse Transcriptase." Molecular Pharmacology, vol. 38, pp. 766-770 (1990).

Goswami, et al., "The Broad Spectrum Antiviral Agent Ribavirin Inhibits Capping of mRNA." Biochemical and Biophysical Research Communications, vol. 89, No. 3, pp. 830-836 (1979).

Kim, et al., "Comparison of Histologic and Quantitative Techniques in Evaluation of Therapy for Experimental Pneumocystis carinii Pneumonia." Antimicrobial Agents and Chemotherapy, vol. 31, No. 2, pp. 197-201 (1987).

Leyseen, et al., "The Predominant Mechanism by Which Ribavirin Exerts Its Antiviral Activity In Vitro against Flaviviruses and Paramyxoviruses Is Mediated by Inhibition of IMP Dehydrogenase." Journal of Virology, vol. 79, No. 3, pp. 1943-1947 (2005).

Miles, et al., "Inactivation of the Amidotransferase Activity of Carbamoyl Phosphate Synthetase by the Antibiotic Acivcin." The Journal of Biological Chemistry, vol. 277, No. 6, pp. 4368-4373 (2002).

Müller, et al., "Virazole (1-$\beta$-$_D$-Ribofuranosyl-1,2,4-Triazole-3-Carboxamide; A Cytostatic Agent." Biochemical Pharmacology, vol. 26, pp. 1071-1075 (1977).

Perrin, et al., "HIV Treatment Failure: Testing for HIV Resistance in Clinical Practice." Science AAAS, vol. 280, No. 5371, pp. 1871-1873 (1998).

Phelps, et al., "A Novel Basis for Capsid Stabilization by Antiviral Compounds." J. Mol. Biol., vol. 254, pp. 544-551 (1995).

Tipples, et al., "Mutation in HBV RNA-Dependent DNA Polymerase Confers Resistance to Lamivudine In Vivo." Hepatology, vol. 24, No. 3, pp. 714-717 (1996).

* cited by examiner

| Lane | 1 | 2 | 3 | 4 | 5 | 6 | 7 | 8 | 9 |
|---|---|---|---|---|---|---|---|---|---|
| Neomycin(4mg/ml) | - | + | - | + | - | + | - | + | - |
| Addition time (h.p.i) | - | 1 | - | 3 | - | 5 | - | 7 | - |

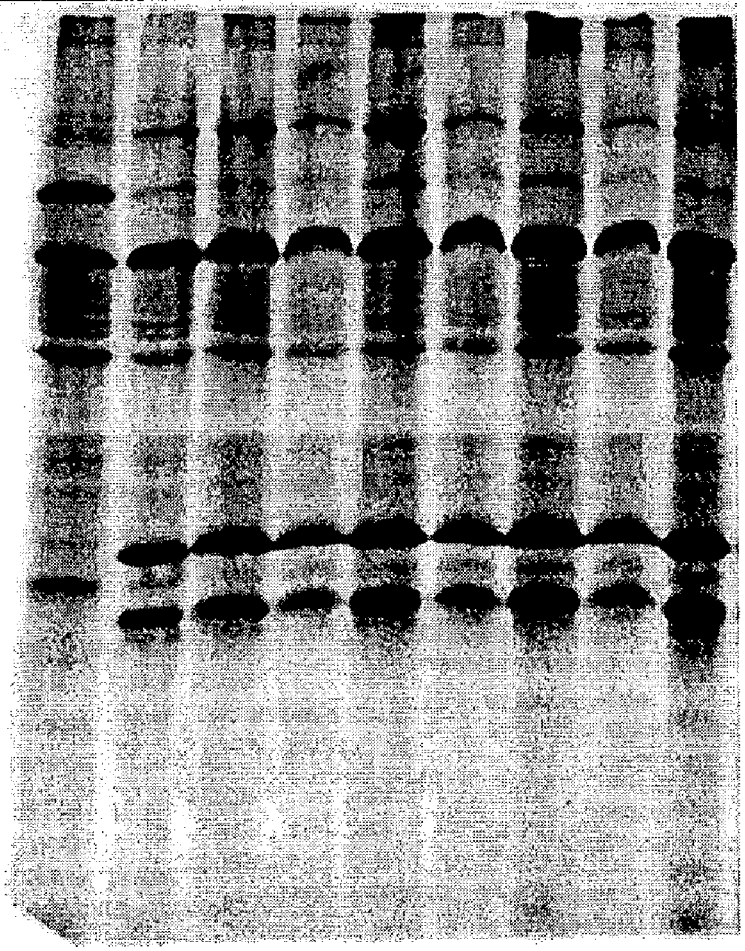

METHODS FOR INCREASING THE SURVIVAL OF AQUATIC ANIMALS INFECTED WITH AN AQUATIC VIRUS

CROSS-REFERENCE TO RELATED APPLICATIONS

This application claims the benefit of U.S. Provisional Application No. 60/336,684 filed Dec. 7, 2001, the content of which is incorporated by reference herein in its entirety, including claims, drawings and structures.

BACKGROUND OF THE INVENTION

1. Field of the Invention

The present invention is directed generally to treating organisms, particularly aquatic organisms susceptible to a virus, such as an aquatic birnavirus infection, by administering compounds that increase the survival the subjects when exposed to or infected with an virus. The invention is directed to a prophylactic/therapeutic method for increasing the survival of aquatic species, particularly fish populations, that may be or are infected with a virus such as an aquatic birnavirus, and more particularly to a composition for the prevention and treatment of infectious pancreatic necrosis virus (IPNV) in fish comprising isoxazol compounds and/or aminoglycoside compounds. The invention is also directed to a prophylactic/therapeutic method for increasing the survival of animal species, particularly poultry and pig populations, that may be or are infected with a virus such as a birnavirus, ortomixovirus, picornavirus and to a composition for the prevention and treatment of infectious bursal disease virus (IBDV) in poultry comprising isoxazol compounds and/or aminoglycoside compounds.

2. Background

It is estimated that fish diseases cost twenty to thirty cents for each dollar spent rearing fish in the United States. Although fish pathogens include fungal, protozoan, and bacterial agents, it is the viral diseases that most concern fish farmers, hatchery managers, and scientists because they are largely uncontrollable. Fish are susceptible to a variety of viral infections and diseases. Such viruses include IPNV, pillar cell necrosis virus (PCNV), infectious hematopoietic necrosis virus (IHNV), viral hemorrhagic septicemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anemia virus (ISAV), as well as others in the following families: Birnaviridae, Rhabdoviridae, Iridoviridae, Reoviridae, Ortomixovirus, and Picornavirus. For example, aquatic birnaviruses infect over 63 marine and fresh water organisms such as fish, shrimp and other crustaceans, oysters and other mollusks. The aquatic birnavirus, IPNV, is the causative agent of pancreatic disease in fish. Other birnaviridae species are known, such as IBDV, tellina virus and oyster virus.

IPNV and IBDV are members of the Birnaviridae family. They are an unenveloped icosahedric virus of approximately 60 nm in diameter with a genome consisting of two segments of double-stranded RNA.

Infectious pancreatic necrosis virus (IPNV) is a contagious viral disease in a variety of aquatic animals. In fish, IPNV causes morbidity and mortality in rainbow trout, Atlantic salmon, Pacific salmon, brook trout and other salmonids, especially fry, smolt and juvenile stages. IPNV is capable of infecting a number of different hosts and has a worldwide presence. Pilcher et al., Crit. Rev. Microbiol. 7:287 (1980), the contents of which are incorporated by reference in its entirety. IPNV has been isolated in a variety of aquatic animal species throughout the world, including various trout and salmon species, carp, perch, pike, eels, char, mollusks and crustaceans. Examples of species of fish and crustaceans/shellfish from which IPNV and viruses similar to IPNV have been isolated is found in Table 1. For example, IPNV has been found in such aquatic animals as Atlantic Salmon, farmed rainbow trout *Oncorhynchus mykiss,* wild flounder *Rhombosolea tapirina,* cod *Pseudophycis* sp., spiked dogfish *Squalus megalops* and ling *Genypterus blacodes.* Crane et al., Dis. Aquat. Organ. 43:1 (2000). IPNV has been isolated from salmonid and non-salmonid species of fish that lack pathogenic symptoms.

Infectious bursal disease virus (IBDV) is also a contagious viral disease in a variety of birds. IBDV affects the bursa of Fabricius, an organ that produces lymphocytes that help protect birds against disease and illness. IBDV attacks the bursa, killing lymphoid cells and suppressing the birds' immune systems. Clinical symptoms of IBDV include diarrhea, weight depression, paleness, and lameness. These symptoms result in increased condemnations of bird carcasses, above average mortality, and poor feed conversion and weight gain. IBDV causes serious problems for commercial poultry producers throughout the world, costing millions of dollars annually in production losses and treatment costs, and amounting to over a hundred million dollars in losses each year worldwide. IBDV is able to rapidly produce mutated viruses, called variant strains, that are resistant to vaccines.

TABLE 1

Species of Fish and Crustaceans / Shellfish From Which IPNV and Viruses Similar to IPNV Have Been Isolated

| Scientific Name | Common Name (English or Spanish) |
|---|---|
| Salmon | |
| *Hucho hucho* | Danube Salmon |
| *Oncorhynchus gorbuscha* | Pink Salmon |
| *Oncorhynchus keta* | Chum Salmon |
| *Oncorhynchus kisutch* | Coho Salmon |
| *Oncorhynchus masou* | Cherr Salmon |
| *Oncorhynchus mykiss* | Rainbow Trout |
| *Oncorhynchus nerka* | Sockeye Salmon |
| *Oncorhynchus rhodurus* | Amago salmon |
| *Oncorhynchus tshawytscha* | Chinook Salmon |
| *Salmo clarki* | Cutthroat trout |
| *Salmo gairdneri* | Rainbow trout |
| *Salmo salar* | Atlantic Salmon |
| *Salvelinus alpinus* | Arctic charr |
| *Salvelinus namaycush* | Lake trout |
| *Salvelinus pluvius* | Japanese chare, white spotted |
| *Thymalus thymalus* | Grayling |
| Additional Fish | |
| *Abramis braxa* | Bream |
| *Alosa aestivalis* | Blueback herring |
| *Alosa sapidissima* | American shad |
| *Anguilla anguilla* | European eel |
| *Anguilla japonica* | Japanese eel |
| *Barbus barbus* | Barbel |
| *Blicca djoerkna* | Silver bream |
| *Brachydanio rerio* | Zebra danio |
| *Brevoortia tyrannus* | Atlantic menhaden |
| *Carassius auratus* | Goldfish |
| *Carassius carassius* | Crucion carp |
| *Catostomus commersoni* | White sucker |
| *Chondrostoma nasus* | Sheap |
| Cobitis sp. | Spined bach |
| *Cyprinus carpio* | Carp |
| *Dicentrarchus labrax* | Bass (sea bass) |
| *Esox lucius* | Northern pike |

TABLE 1-continued

Species of Fish and Crustaceans / Shellfish
From Which IPNV and Viruses Similar to IPNV Have Been Isolated

| Scientific Name | Common Name (English or Spanish) |
| --- | --- |
| *Esox niger* | Chain pickerel |
| *Lampetra fluviatilus* | River Lamprey |
| *Leistomus xanthurus* | Spot |
| *Leuciscus rutilus* | Roach |
| *Menidia menidia* | Atlantic Silverside |
| *Morone saxatilis* | Striped Bass |
| *Oxyeleotris matmoratus* | Marble Globy |
| *Paralichthys lethostigma* | Southern flounder |
| *Perca fluviatilis* | Redfin Perch |
| *Peudorasbora parva* | Gobio |
| *Phoxinus phoxinus* | Minnow |
| *Scardinius arythophthalmus* | Leucisco |
| *Scophtalmus maximus* | Turbot |
| *Seriola quinquerodiata* | Japanese Amber Jack |
| *Solea solea* | Common sole |
| *Stizostedion vitreum vitreum* | Pungent Throat |
| *Symphysodon discus* | |
| *Tilapia mossambica* | Aucun |
| *Trinectes maculatus* | |
| Shellfish / Crustaceans | |
| *Carcinus masnas* | Shore Crab |
| *Crassostrea gigas* | Japanese oyster |
| *Crassostrea virginica* | Eastern oyster |
| *Littorina littorea* | Common periwinkle |
| *Mercenaria mercenaria* | Hard clam |
| *Mytilus edulis* | Common mussel |
| *Ostrea edulis* | Native oyster |
| *Patella vulgata* | Common limpet |
| *Penasus japonicus* | |
| *Tellina tenuis* | Thin tellis |

In survivors of an IPNV epizootic, the virus persists and can cause severe growth retardation in the individual fish that exhibit virus persistence. McKnight et al., Br. Vet. J. 132: 76 (1976). In smolts, IPNV produces considerable necrosis or inflammation of the pancreas. Acute disease has been reported primarily in a limited number of salmonid species, such as trout and salmon. Many of these species are of great economic importance. Because mortality can be as high as 90 percent, an IPNV outbreak in a hatchery can be an economic disaster. Pilcher et al., Crit. Rev. Microbiol. 7:287 (1980).

The most susceptible age for IPNV infection in fish is in young fish, especially those that are two- to four-month old, in which such infections result in high mortality. Wolf et al., U.S. Dept. Int. Bur. Sport Fish and Wildlife Fish Disease Leaflet 1:14 (1966); Frantsi et al., J. Wildlife Dis. 7:249 (1971). In trout, IPNV usually attacks young fry about five to six weeks after their first feeding. IPNV is known to affect fish in their first year in salt water and to spread rapidly in farmed fish held in sea cages. Affected fish are thin, anorexic and lethargic with a tendency to congregate in cage corners and to fail to maintain a horizontal position. Ferguson et al., J. Fish Dis. 9:95 (1986). The affected fish are darker than usual, have slightly bulging eyes and often have swollen bellies. At the beginning of an outbreak, large numbers of slow, dark fry are seen up against water outflows, and fish are seen "shivering" near the surface. The shivering results from a characteristic symptom of the disease, a violent whirling form of swimming in which the fish rotate about their long axis. If the internal anatomy of the affected fish is examined, a characteristic white mucus is seen in the stomach. The pancreas appears to be the primary target organ for the virus. McKnight et al., Br. Vet. J. 132:76 (1976).

After an IPNV outbreak, the surviving fish generally become carriers of the virus. Fish that carry the virus are a serious problem for the aquaculture industry because the only control method currently available for eliminating the virus in carrier fish is complete destruction of these fish. Several factors appear to influence the severity of infection and the subsequent establishment of the carrier state. These factors include age, species, and water temperature. Surviving carriers shed infectious IPNV for the remainder of their lifetime, which is detectable in their fecal matter and sex products. Billi et al., J. Fish. Res. Bd. Can. 26:1459 (1969); Yamamoto, Can. J. Micro. 21:1343 (1975); and Reno et al., J. Fish. Res. Bd. Can. 33:1451 (1978).

The persistence of the virus in carrier fish appears to be the result of continued virus production by a small number of infected cells in certain organs. Hedrick, Ph.D. Thesis, "Persistent Infections of Salmonid Cell Lines with Infectious Pancreatic Necrosis Virus: A Model for the Carrier State in Trout," Oregon State University, 1980. For IPNV, there are at least 9 type strains of Serogroup A and 4 other representative strains of Serotype A1. IPNV Serotype A1 is the predominant aquatic birnavirus and IPNV serotype in the United States. The family Birnaviridae describes and classifies a group of viruses, birnaviruses, which carry a bisegmented double-stranded RNA genome as their prominent characteristic; the two segments are called segment A and B. The RNA is enclosed in a non-enveloped icosahedral capsid, about 60 nm in diameter, which is arranged as a single shell. The two main representatives of this virus family are the infectious pancreatic necrosis virus of fish (IPNV) and the causative agent of infectious bursal disease of chickens (IBDV). The RNA of both IPNV and IBDV is covalently linked to a high molecular weight polypeptide, which is approximately 100 kDa. Birnaviruses have at least four structural proteins: named VP1, VP2, VP3 and VP4. The sequence of VP1, VP2, VP3 and VP4 allowed the construction of the genomic map of both IPNV and IBDV. See Dobos, P., *The molecular biology of IPNV,* Ann. Rev. Fish Diseases, 5:25-54 (1995).

The IPNV viral genome is contained within a non-enveloped icosahedral capsid that is approximately 60 mn in diameter. The larger "A" segment has a molecular weight of $2.5 \times 10^6$ Daltons (Da) and encodes at least three proteins. Their order in the genome, from the N (5') terminus, is β(VP2) (approximately 54 kDa, major capsid protein); γ2 (NS) (an approximately 27.5 kDa nonstructural protein having proteolytic activity); and γ1 (VP3) (an approximately 31 kDa minor capsid protein. Chang et al., Can. J. Microbiol. 24:19 (1978); Huang et al., J. Virol. 60:1002 (1986). These proteins are encoded on a single mRNA within the infected cell. Mertens et al., Nature 297:243 (1982). Genome segment A of IPNV contains the a large open reading frame (ORF) encoding a 106 kDa polyprotein, which has the structure: NH2-preVP2-VP4 protease-VP3-COOH. The polyprotein is cotranslationally cleaved by a virus-encoded protease, to generate preVP2 (pVP2) and VP3. The VP2 is further cleaved during viral maturation to produce VP2. Genome segment A contains an additional small ORF, which overlaps the amino terminus of the polyprotein ORF and is in a different reading frame. This small ORF encodes a 17 kDa arginine-rich minor polypeptide, which can be detected in IPNV infected cells. The product of genome segment B is a minor internal polypeptide VP1. VP1 is the putative virion-associated RNA-dependent RNA polymerase. VP1 is present in the virions in two forms: (1) as a free polypeptide and (2) as a genome-linked protein (VPg).

The genomic maps established for IBDV are similar to the IPNV genomic map described above, which indicates that the their genomic organization is characteristic of birnaviruses in general. Thus, the unique features of birnaviruses are: (i) a genome segment A is both structurally and functionally bicistronic; (ii) production of a polyprotein that is cleaved by a virus-encoded protease; and (iii) the presence of a genome-linked protein (VPg). Furthermore, both genome segment A and genome segment B contain noncoding regions of considerable size at both of their ends. These noncoding sequences may be important for polymerase recognition, translation initiation and possibly genome packing. In addition, segment A from IPNV contains inverted terminal repeats of 14 nucleotides, which are similar to those reported for segment A of IBDV. See,Encyclop. Vir., Ed. R. G. Webster and A. Granosf, Academic Press (1995) at 143-149.

A few antiviral compounds used to treat human viruses have been tested for their ability to block IPNV infection in vitro. They are: virazole (Savan et al., J. Fish Dis. 3:437 (1980); ribavirin, pyrazofurin and EICAR (5-ethynyl-1-β-ribofuranosylimidazole-carboxamide) (Migus et al., J. Gen. Virol. 47:47 (1980); Jashés et al., Antiviral Res. 29:309 (1996)). Although ribavirin was shown to inhibit IPNV replication in vitro, it had no efficacy in vivo. Migus et al., J. Gen Virol. 47:47 (1980). When EICAR was given to rainbow trout and Coho salmon fry on the first day after the fry were experimentally infected with IPNV, fewer deaths occurred among the infected fry. Moya et al., Antiviral Res. 48: 125 (2000).

In vivo assays establish the ability of the candidate compound to inhibit viral replication in vivo and/or improve morbidity and mortality. This was shown for ribavirin, which efficiently inhibits IPNV replication in vitro, yet not in vivo. Migus et al., supra (1980); Savan et al., J. Fish. Dis. 3: 437 (1980).

In order to decrease the prevalence of disease and increase the yields of farmed fish, a considerable number of antibiotics and chemicals are used to treat the water during fish farming. Examples of such antibiotics and chemicals are listed in Table 2.

TABLE 2

Chemicals Administered in Fish Farming
(by English or Spanish name)

| | |
|---|---|
| Acetic acid | Griscofulvin |
| Acriflavine | Hydroxyl methyl pyridine |
| Bacitracin | Iodosphoresphorus 1.7% |
| Lime | activity |
| Sodium cyanate | Sodium hypochorite 130% |
| Chioramphenicol | Isoniacide |
| Chiorotetracycline | Kanamicine |
| Sodium Chloride | Levamisole |
| Dibromide | Nalidixic acid |
| dichiormethyldimethyl | Neomycin |
| phosphate | Organophosphates |
| Potassium Dichromatc | Oxitetracycline |
| (Potassium Bichromate) | Oxoline acid |
| Di-n-butyl tin oxide | Potassium Permanganate |
| Dimetridazole | Praziquantel |
| Dibromideethylene | Ammonium quaternary salt |
| dipirididilene | Chloride toluene sulfonic |
| Eritromicine | sodium |
| Hexaclorinebenzene isomer | Sulfaguanidine |
| "Febantel" Fenotiacine | Sulfamerazine |
| Flumeuine | Tetracycline |
| Gentamicin | Trimetoprim |
| Gentian Violet | Vitamin C |
| Green malachite | |

Other than the destruction of infected stocks and the decontamination of hatchery facilities, there is no current treatment comprising an isoxazol compound and/or an aminoglycoside compound to combat viral infections in an aquaculture setting that is capable of increasing the survival of aquatic animals susceptible to the viral infection. There is also a need for methods and compositions comprising isoxazol compounds and/or aminoglycoside compounds that can be administered prior to, during, and for periods of time after the susceptible species is exposed to a virus. Further, there is a need for a treatment to combat a virus in an aquaculture setting that employs an isoxazol compound and/or an aminoglycoside compound that is stable in solution. Also, there is no current aquatic food composition containing a isoxazol compound that is capable of increasing the survival of aquatic animals susceptible to a viral infection before, during, and for periods of time after the susceptible species is exposed to the virus. Accordingly, there remains a need for a method of increasing the survival of aquatic animals exposed to or infected with a virus where the method includes administering an isoxazol compound and/or an aminoglycoside compound. Hence, there is a need for a method of administering an isoxazol compound and/or an aminoglycoside compound to animals, including aquatic animals, susceptible to a viral infection in order to increase their survival when exposed to or infected with a virus.

Other than the destruction of infected stocks and the decontamination of hatchery facilities, there is no current treatment to combat IPNV in an aquaculture setting that is capable of increasing the survival of aquatic animals susceptible to IPNV infection. Also, there is no current treatment to combat IBDV in manner that is capable of increasing the survival of animals susceptible to IBDV infection. There is also a need for methods and compounds that can be administered prior to, during, and for periods of time after the susceptible species are exposed to IPNV or IBDV. Further, there is no current treatment to combat IPNV in an aquaculture setting that employs a compound that is stable in solution, particularly an isoxazol compound. Also, there is no current aquatic food composition containing a compound capable of increasing the survival of aquatic animals susceptible to IPNV infection before, during, and for periods of time after the susceptible species is exposed to IPNV. Also, there is no current food composition containing a compound capable of increasing the survival of animals susceptible to IBDV infection before, during, and for periods of time after the susceptible species is exposed to IBDV. Accordingly, there is a great need for a method of increasing the survival of animals, including aquatic animals, exposed to or infected with IPNV and IBDV, despite the need for such methods. Hence, there is a need for a method of administering a compound to aquatic animals susceptible to IPNV infection that will increase their survival when exposed to or infected with IPNV. Further, there is a need for a method of administering a compound to animals susceptible to IBDV infection that will increase their survival when exposed to or infected with IBDV.

SUMMARY OF THE INVENTION

It therefore is an object of the present invention to provide a method of increasing the survival of an animal susceptible to infection by, exposed to or infected by, a virus selected from the group consisting of: IPNV, IBDV, pillar cell necrosis virus (PCNV), infectious hematopoietic necrosis virus (IHNV), viral hemorrhagic septicemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anemia virus (ISAV), tellina virus, oyster virus, a Birnaviridae virus, a Rhabdoviridae virus, an Iridoviridae virus, a Reoviridae virus, a Picomaviridae virus, and an Ortomixoviridae virus, by administering an effective amount of an isoxazol compound and/or aminoglycoside compound to the animal.

It is a further object of this invention to provide a method of treating an aquatic animal susceptible to infection from a virus selected from the group consisting of: IPNV, pillar cell necrosis virus (PCNV), infectious hematopoietic necrosis virus (IHNV), viral hemorrhagic septicemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anemia virus (ISAV), tellina virus, oyster virus, a Birnaviridae virus, a Rhabdoviridae virus, an Iridoviridae virus, a Reoviridae virus, a Picomaviridae virus, and an Ortomixoviridae virus, comprising feeding the fish or other animal a food that contains an effective amount of an isoxazol compound and/or aminoglycoside compound.

It is yet another object of the present invention to provide a method of raising fish and other animals that comprises administering an effective amount of an isoxazol compound an/or aminoglycoside compound.

In another object of the present invention, the isoxazol compound employed in the method and the compositions, including food compositions, is an isoxazol compound that is selected from the group consisting of acivicin and acivicin analogue compounds having the Formula

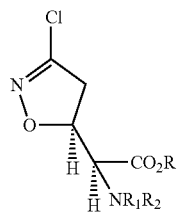

wherein R is selected from the group consisting of hydrogen and alkyl of from 1 to 8 carbon atoms; $R_1$ and $R_2$ are different and are selected from the group consisting of hydrogen, a compound of the Formula

or when taken together with the nitrogen atom form a group having the Formula

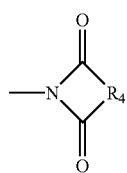

wherein $R_3$ is alkyl of from 1 to 8 carbon atoms, inclusive; and $R_4$ is selected from the group consisting of (a) a compound having the Formula

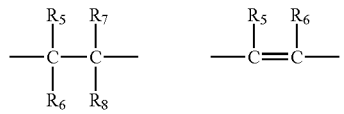

wherein $R_5$, $R_6$, $R_7$ and $R_8$ are selected from the group consisting of hydrogen and alkyl of from 1 to 5 carbon atoms, inclusive (b) a compound of the Formula

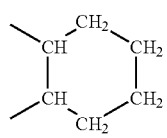

(c) orthointerphenylene, and (d) substituted orthointerphenylenes with the proviso that other than when $R_1$ and $R_2$ forms a ring with the nitrogen atom one of $R_1$ and $R_2$ must always be hydrogen, preferably R and $R_1$ are hydrogen and $R_2$ is alkoxycarbonyl; most preferably $R_2$ is L-butyloxycarbonyl and the compound is 3-chloro-2-[[(1,1-dimethoxy)carbonyl]amino[-4,5-dihydro-5-isoxazoleacetic acid; also preferably R is hydrogen and $R_1$ and $R_2$ together with the nitrogen atom form the group of the Formula

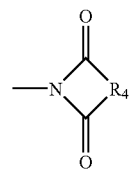

more preferably $R_4$ is orthointerphenylene and the compound is phthalyl-(αS, 5S)-α-amino-3-chloro-4,5-dihydro-5-isoxazolacetic acid; as well as racemic mixtures and optically active isomers of compounds having the Formula

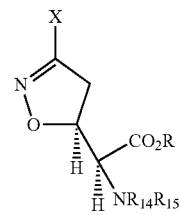

wherein R is selected from the group consisting of hydrogen, alkyl of from 1 to 8 carbon atoms, inclusive, halogenated alkyl of from 1 to 3 halogen atoms, and 1 to 5 carbon atoms, inclusive, aralkyl of from 7 to 20 carbon atoms, inclusive; and substituted aralkyl of from 7 to 20 carbon atoms, inclusive. X is selected from the group consisting of bromine, chlorine, fluorine and iodine, —$OR_1$, —$SR_1$, and —NR'R" wherein $R_1$ is selected from the group consisting of alkyl of from 1 to 12 carbon atoms, inclusive, aryl of from 6 to 20 carbon atoms, inclusive; aralkyl of from 7 to 20 carbon atoms; inclusive; R' and R" are the same or different and are selected from the group consisting of hydrogen and alkyl of from 1 to 8 carbon atoms; $R_{14}$ and $R_{15}$ are selected from the group consisting of hydrogen, a compound having the Formula

or when taken together with the nitrogen atom or the group having the Formula

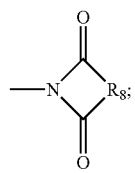

wherein $R_6$ is an alkyl of from 1 to 8 carbon atoms, inclusive, halogenated alkyl of from 1 to 5 carbon atoms, inclusive, and 1 to 3 halogen atoms, inclusive, aralkyl of from 7 to 20 carbon atoms inclusive, and substituted aralkyl of from 7 to 20 carbon atoms, inclusive, $R_7$ is selected from the group consisting of alkyl of from 1 to 12 carbon atoms, inclusive, aryl of from 6 to 20 carbon atoms, inclusive, aralkyl of from 7 to 20 carbon atoms, inclusive, and substituted aralkyl of from 7 to 20 carbon atoms, inclusive; and $R_8$ is selected from the group consisting of a compound having the Formula $$-\overset{R_9}{\underset{R_{10}}{C}}-\overset{R_{11}}{\underset{R_{12}}{C}}-$$

wherein $R_9$, $R_{10}$, $R_{11}$ and $R_{12}$ are selected from the group consisting of hydrogen and alkyl of from 1 to 5 carbon atoms, inclusive, (b) a compound having the Formula

[cyclohexane structure]

(c) orthointerphenylene compounds having the Formula

[ortho-disubstituted benzene structure]

and (d) substituted orthointerphenylene with the proviso that when R, $R_{14}$ and $R_{15}$ are all hydrogen, X cannot be chlorine, and the further proviso that when $R_{14}$ and $R_{15}$ are both hydrogen and R8 is orthointerphenylene, R cannot be hydrogen or alkyl of from 1 to 8 carbon atoms.

In another object of the present invention, the isoxazol compound employed in the method and the compositions, including food compositions, is selected from the group consisting of an isoxazol derivative compound having the Formula

[isoxazole structure with substituents $R_1$, $R_5$, Y—O—phenyl ($R_2$, $R_3$), oxazole with $R_4$]

wherein: $R_1$ is alkyl, alkoxy, hydroxy, cycloalkyl, hydroxyalkyl, alkoxyalkyl, hydroxyalkoxy, alkylthioalkyl, alkylsulfinylalkyl, alkylsulfonylalkyl, aminoalkyl, alkylaminoalkyl, dialkylaminoalkyl, alkoxycarbonyl, carboxy, or cyanomethyl; Y is alkylene of 3 to 9 carbon atoms, $R_2$ and $R_3$ independently are hydrogen, alkyl, alkoxy, halo, cyano, trifluoromethyl and nitro; $R_4$ is alkoxy, hydroxy, halomethyl, dihalomethyl, trihalomethyl, dihaloethyl, cycloalkyl, heterocyclyl, alkoxycarbonyl, hydroxyalkyl, alkoxyalkyl, alkanecarbonyloxyalkyl, cyano, halo, thioalkyl, alkylthioalkyl, alkylthio, thio, 2,2,2-trifluoro-ethyl, (4-methylphenyl) sulfonyloxymethyl, N=Q or CON=Q, wherein N=Q is amino, alkylamino or dialkylamino; $R_5$ is hydrogen or halo or alkyl.

A further object of the present inventions is to provide the methods and compositions, including food compositions, having an isoxazol compound selected from the group consisting: of an isoxazol derivative compound having the Formula

[isoxazole structure with R, Z, Y—O—phenyl ($R_1$, $R_2$)—Het]

wherein: Y is an alkylene bridge of 3-9 carbon atoms; Z is N; R is hydrogen or lower-alkyl of 1-5 carbon atoms, with the proviso that when Z is N, R is lower-alkyl; $R_1$ and $R_2$ are hydrogen, halogen, lower-alkyl, lower-alkoxy, nitro, lower-alkoxycarbonyl or trifluoromethyl; and Het is selected from specified heterocyclic groups, unsubstituted 1,3,4-oxadiazol-2-yl and unsubstituted 1,2,4-oxadiazol-5-yl.

Another object of the present invention is to provide a method of increasing the survival of birnavirus-susceptible, exposed and/or infected aquatic and other animals, by administering an effective amount of a compound to the animal, where the compound is any of the following: neomycin, paramomycin, streptomycin, tobramycin, dibekacin, kanamycin, amicacin, gentamycin, sisomycin, netilmycin, lividomycin, ribocamycin, adenine analogues, and guanine analogues. When neomycins are used to increase the survival of the birnavirus-infected aquatic or other animals, the neomycins are used in a manner and/or composition that achieve the increased survival by mediating its effect on the virus infection; for example, by inhibiting RNA synthesis of the virus to increase the survival of the virally infected animals. It is therefore an object of the present invention to provide a method of increasing the survival of animals and aquatic species infected with birnavirus infection by treating them with a chemical compound capable of inhibiting viral replication, such as isoxazol or neomycin.

A further object of the instant invention is directed to a method of treating an aquatic animal or other animal susceptible to IPNV or IBDV infection, exposed to and/or infected with IPNV or IBDV, comprising feeding food that contains an effective amount of a compound selected from the following: neomycins, paramomycin, streptomycin, tobramycin, dibekacin, kanamycin, amicacin, gentamycin, sisomycin, netilmycin, lividomycin, ribocamycin, adenine analogues, and guanine analogues.

In these objects of the invention, the administering can be accomplished by methods known in the art, including any of the following methods: introducing the compound into the aquatic environment; including the compound in food; and injecting into the animal the compound dissolved in a pharmaceutically acceptable carrier.

In another object of the present invention, the compound employed is acivicin or an isoxazol derivative that is a WIN compound. In another preferred embodiment, the isoxazol compound is stable in solution and/or when wet. A further embodiment of the methods and compositions of the present invention employs the compound in an effective amount that increases survival of the animal from about 10% to about 30%; preferably survival increases from about 10% to about 70%. Another object of the present invention employs a concentration of the isoxazol compound or the aminoglycoside compound that effectively inhibits viral replication in the infected animal. Preferred concentrations also can decrease the viral load/viral titer of the IPNV in a tissue by about 10 to 1000-fold or the load may decrease to between about $10^1$ pfu/ml and $10^3$ pfu/ml. Preferred concentrations that are an effective amount of the isoxazol compound can be from about 7.0 µg/ml to about 30 µg/ml of water in their environment, preferably from about 9.0 µg/ml to about 14.0 µg/ml of water in their environment.

A further object of the methods and compositions of the present invention is directed to poultry and the preferred aquatic animals, which are fish, copepods, cephalopods, crustaceans, shrimp, eels, mollusks, and oysters. Another object of the present invention is directed to the fish to which the instant method and compositions are applied, namely those listed in Table 1. Also, the fish may be selected from fish in the following families: Anguillidae, Bothidae, Caragidae, Cotostomidae, Chichlidae, Clupeidae, Cobitidae, Coregonidae,, Cyprinidae, Esocidae, Moronidae, Paraichthydae, Percidae, Poecilidae, Salmonidae, Salvelinus, Sciaenidae, Thymallidae and the species *Seriola quinqueradiata* (yellowtail), *Scopthalmus maximus* (turbot), *Limanda limanda* (dab), *Hippoglossus hippoglossus* (halibut), *Gadus morhua* (Atlantic Cod), *Misgrunus anguillisaudatus* (loach), and *Esox lucious* (pike); more preferably, the fish is in the Salmonidae or Salvelinus family, including rainbow trout, brook trout, salmon, *Oncorhynchus tshawytscha* (Chinook, King, or Spring), *Oncorhynchus nerka* (Blueback, Red, Sockeye), *Oncorhynchus kisutch* (Coho, Silver), *Oncorhynchus gorbuscha* (Pink), *Onchorhynchus mykiss* (Rainbow trout), *Oncorhynchus keta* (Chum, or Keta), and *Oncorhynchus masou* (Masou, or Cherry).

Yet another object of the present inventions is to provide food and methods employing such food which contain the isoxazol compound and/or aminoglycoside compound. One such preferred composition is a food pellet, which may be a moist pellet.

A further object of the present invention provides an effective amount of the isoxazol compound and/or aminoglycoside compound to slow or stop the progression of disease, such as pancreatic disease.

In other objects of the present inventions, the methods and food compositions are directed to fish weighing from about 0.6 to about 10 grams, fish weighing from about 10 grams to about 200 grams, fish weighing from about 200 grams to about 5000 grams, or greater. In other objects of the present inventions, the methods and food compositions are directed to animals, such as poultry or pigs, weighing from about 0.6 to about 10 grams, or weighing from about 10 grams to about 200 grams, or weighing from about 200 grams to about 5000 grams, or greater.

It is also an object of the present invention to provide such methods in which the administering or feeding can occur: (i) prior to the animal's exposure to and/or infection with the virus; (ii) during the exposure of the animal to and/or infection with the virus; and/or (iii) after the exposure of the animal to and/or infection with the virus; or (iv) any combination of such administration of feeding times.

In another object of the present invention, the administering or feeding can occur: (i) prior to the animal's exposure to and/or infection with a virus; (ii) during the exposure of the animals to and/or infection with a virus; and/or (iii) after the exposure of the animal to and/or infection with to a virus. In a further object of the invention, the administering or feeding can occur: (i) prior to the exposure of the animal to and/or infection with a virus; (ii) during the exposure of the animals to and/or infection with a virus; and/or (iii) after the exposure of the animal to and/or infection with a virus.

It is yet another object of the invention to provide food for the aquatic animals, such as fish food, is in the form of a pellet. Preferably, the food contains an isoxazol compound, preferably acivicin, at a concentration of from about 1 µg to about 100 µg/gram food, preferably from about 5 µg to about 25 µg/gram of food.

Another object of the present invention is to provide a method of increasing the survival of an animal susceptible to infection by a virus selected from the group consisting of: infectious bursal disease virus (IBDV), a Birnaviridae virus, a Rhabdoviridae virus, an Iridoviridae virus, a Reoviridae virus, an Ortomixovirus virus, a Paramixovirus virus, an Arterivirus virus, and a Picornavirus virus comprising administering an effective amount of an isoxazol compound to the animal. In a preferred object of the present invention, the animal is a bird and the virus is infectious bursal disease virus (IBDV). It is a further object of the present invention to provide a method of treating an animal susceptible to IBDV infection by administering an effective amount of an isoxazol compound, in which the administering is by a method selected from the group consisting of: (i) including the compound in food and (ii) injecting into the animal the compound dissolved in a pharmaceutically acceptable carrier. Further, the administering is conducted at a time, such as before; during; after; during and after; before and during; before and during and after; or before and after the animal is exposed to and/or infected by the virus.

It is also an object of the present invention to provide a method where the effective amount is a concentration that decreases the viral load/viral titer of IBDV in a tissue of the animal; as examples, the effective amount can be: a concentration that decreases the viral load/viral titer of IBDV in a tissue of the animal by from about 10-fold to about $10^4$-fold or an amount that slows or stops the progression of IBDV disease. The administering can occur after the clinical signs of IBDV are detected, after the detection of IBDV in tissue of the animal, and/or after the detection of increased mortality or decreased survival in the animal.

It is yet another object of the present invention to provide an animal feed composition containing an isoxazol compound, such as acivicin.

Other objects, features and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

SDS-PAGE and autoradiography. The non infected cell samples were also included in lanes 2, 3, 6, 7, and 8. The migration of IPNV polypeptides is indicated.

Figure 3A:
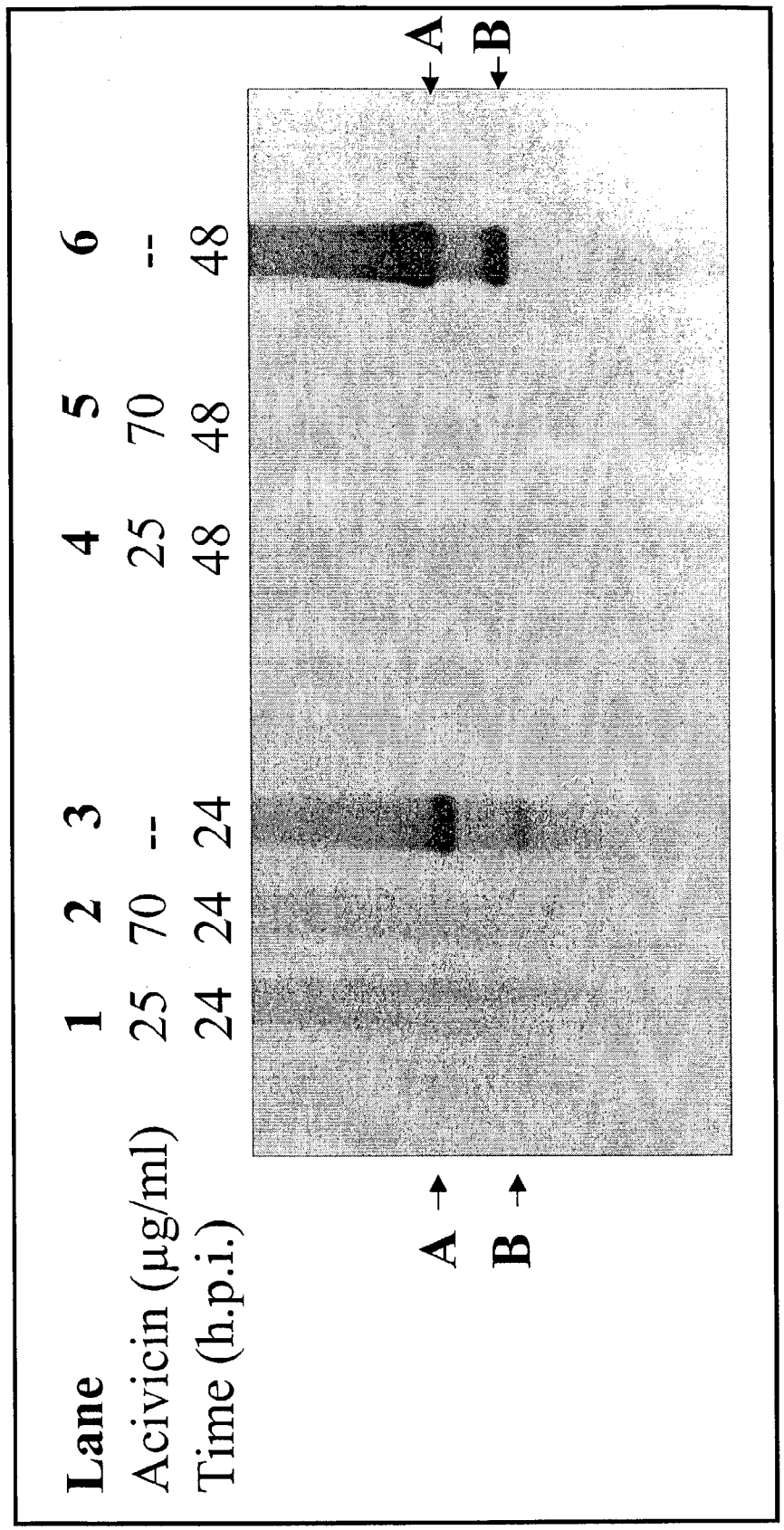
Figure 3B:
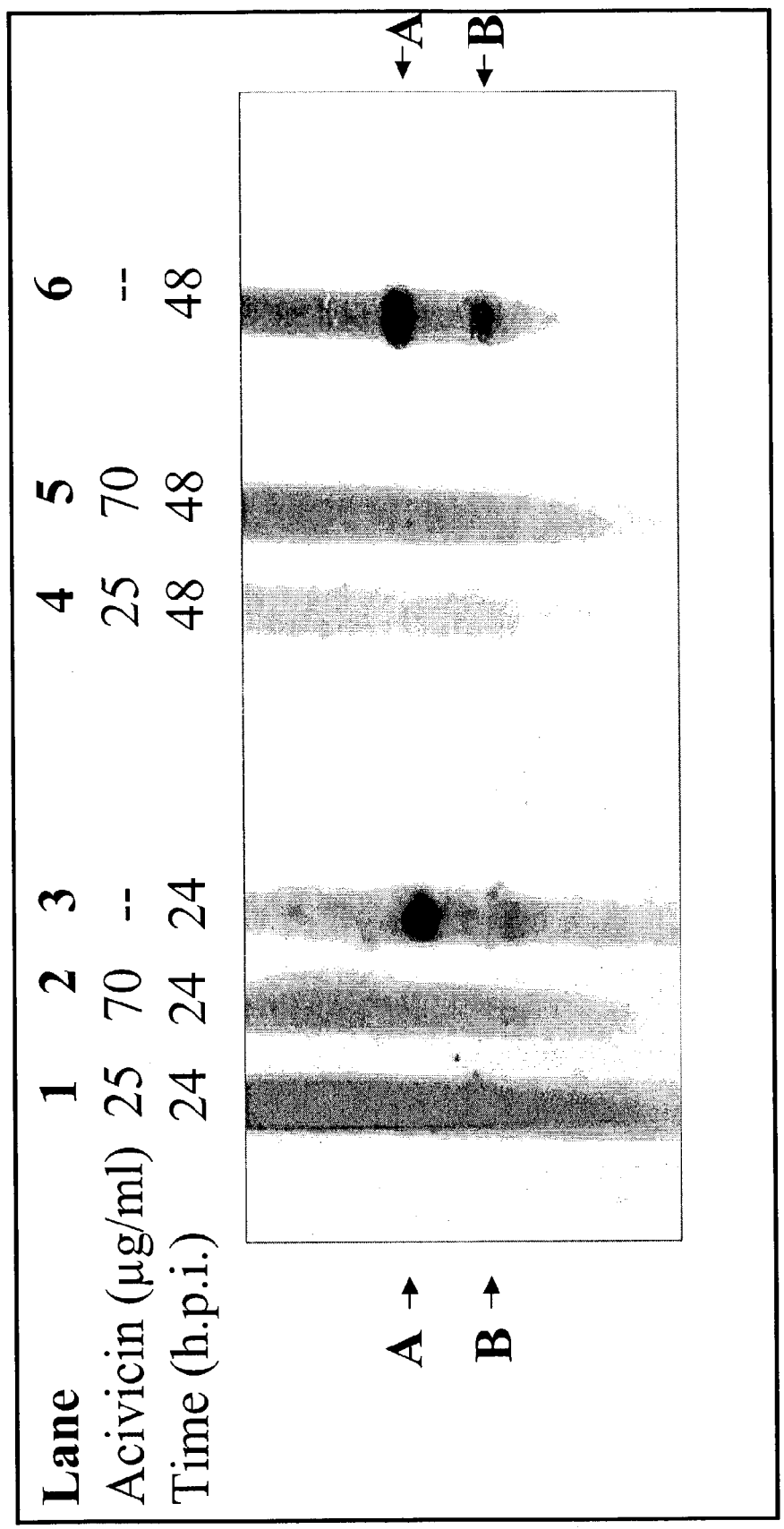

FIGS. 3A and 3B are autoradiographs showing the effect of acivicin on IPNV particle formation.

In FIG. 3A, monolayers of CHSE-214 cells were infected with IPNV either in the absence of acivicin (lanes 3 and 6); or in the presence of 25 µg/ml acivicin (lanes 1 and 4); and in the presence of 70 µg/ml acivicin (lanes 2 and 5). The acivicin antiviral compound was added at the time of infection (zero h.p.i.). The cells were incubated at 15° C. At 2 hours post-infection, 50 µCi/ml of [$^{35}$S]-methionine was applied to the cells. At 24 h.p.i. (lanes 1, 2, and 3) and 48 h.p.i. (lanes 4, 5, and 6), the particles were harvested, concentrated by ultracentrifugation, and partially purified through a sucrose gradient. The viral particles were then subjected to electrophoresis in 0.8% Tris-glycine agarose gels and autoradiography. The migration of the IPNV particles is indicated.

In FIG. 3B, monolayers of CHSE-214 cells were infected with IPNV in the absence of acivicin (line 3 and 6); in the presence of 25 µg/ml acivicin (lanes 1 and 4); and in the presence of 70 µg/ml acivicin (lanes 2 and 5). The same procedures described for FIG. 3A were followed except that at the time of infection, 50 µCi/ml of [$^{32}$P]-orthophosphoric acid were added.

Figure 4:
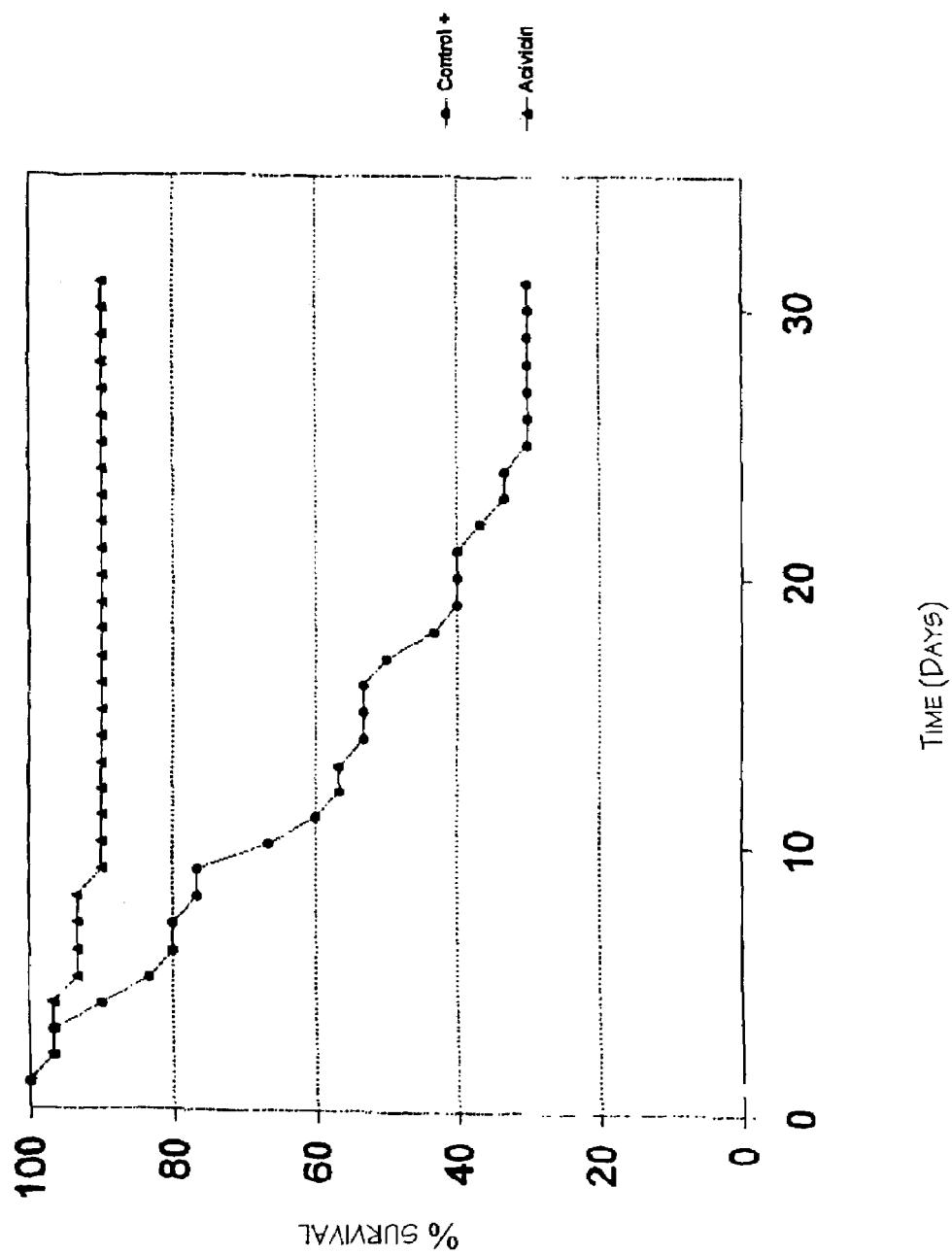

FIG. 4 is a graph showing the effect of acivicin treatment on the survival of rainbow trout fry naturally infection with IPNV. The fish were followed for 30 days starting at day one of the acivicin treatments, to detect and document deaths. The data are presented in terms of percent survival:

●---●: untreated naturally infected fish, positive control.

σ--σ: naturally infected fish treated with 9 µg/ml of Acivicin.

Figure 5:
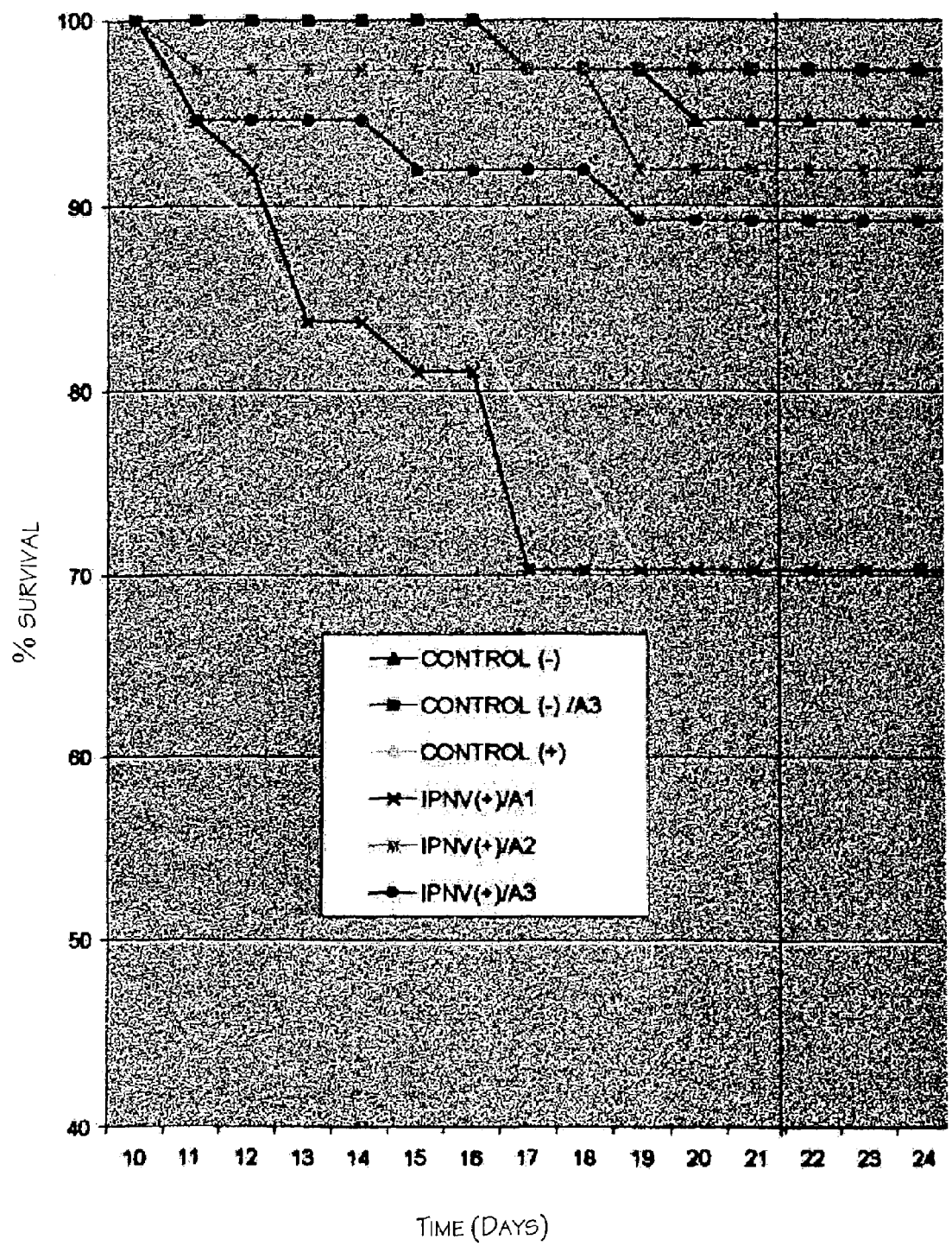

FIG. 5 is a graph showing the effect of various concentrations of acivicin treatments on the survival of Atlantic salmon fry following infection with IPNV. On day 0, the fish are infected with $10^4$ pfu/ml of IPNV. Starting nine days post-infection, the fish are treated daily by immersion for 2 hours in a bath containing 9 µg/ml of acivicin. This daily treatment in acivicin continued through day 21 post-infection. The fish were followed for 36 days post-infection to document deaths, the data of which are presented graphically in terms of percent survival. The FIG. 5 legend indicates:

(▲-▲) "CONTROL (−)"=negative control, non infected fish;

(◙-◙) "CONTROL (−)/A3"=negative control, non infected fish treated with 14 µg/ml of acivicin;

(Δ-Δ) "CONTROL (+)"=positive control, untreated infected fish;

(X-X) "IPNV(+)/A1"=infected fish treated with 7 µg/ml of acivicin;

(x-x) "IPNV(+)/(A2)"=infected fish treated with 10.8 µg/ml of acivicin; and (●-●) "IPNV(+)/(A3)"=infected fish treated with 14 µg/ml of acivicin.

Figure 6A:
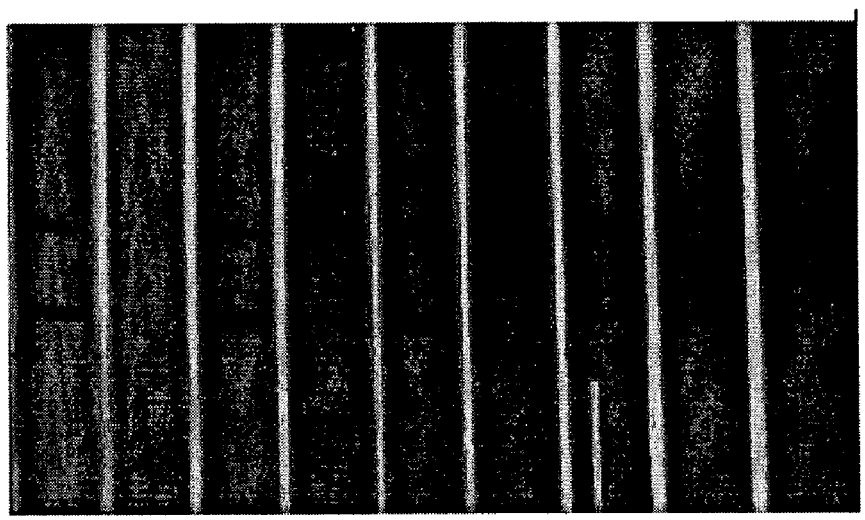

FIG. 6A is a photograph of a 7% polyacrylamide gel showing the effect of neomycin on IPNV genomic RNA synthesis. Monolayers of Chinook salmon embryo cell line 214 (CHSE-214) cells were infected with IPNV either in the absence (lanes 3,5,7 and 9) of neomycin, or in the presence of neomycin at 4 mg/ml (lanes 2, 4, 6 and 8). Neomycin was added to the cells at 1, 3, 5 and 7 hours post-infection (h.p.i.), (lanes 2, 4, 6 and 8) respectively, and the cells were incubated at 15° C. At 24 hours post-infection the cells were harvested, RNA extracted therefrom, and analyzed by 7% polyacrylamide gel electrophoresis (PAGE) stained with silver nitrate. Lane 1 shows a control of IPNV genomic RNA. The data show that Neomycin inhibited the IPNV RNA synthesis FIG. 6B is an autoradiograph showing the effect of neomycin on IPNV polypeptide synthesis. Monolayers of CHSE-214 cells were infected with IPNV either in the absence (lanes 3,5,7 and 9) or presence of neomycin at 4 mg/ml (lanes 2, 4, 6 and 8). Neomycin was added at 7, 5, 3 and 1 hour post-infection (h.p.i.), (lanes 2, 4, 6 and 8) respectively, and the cells were incubated at 15° C. At four hours post-infection, 50 µCi/ml of [$^{35}$S]-methionine was applied to the cells. At 24 h.p.i. 100 µl of a protein disruption solution was added to the cell monolayers. The polypeptides from the disrupted cells were analyzed by 15% SDS-PAGE and autoradiography. Lane 1 is a control of uninfected CHSE-214 cells. Neomycin does not inhibit IPNV polypeptide synthesis.

Figure 7:
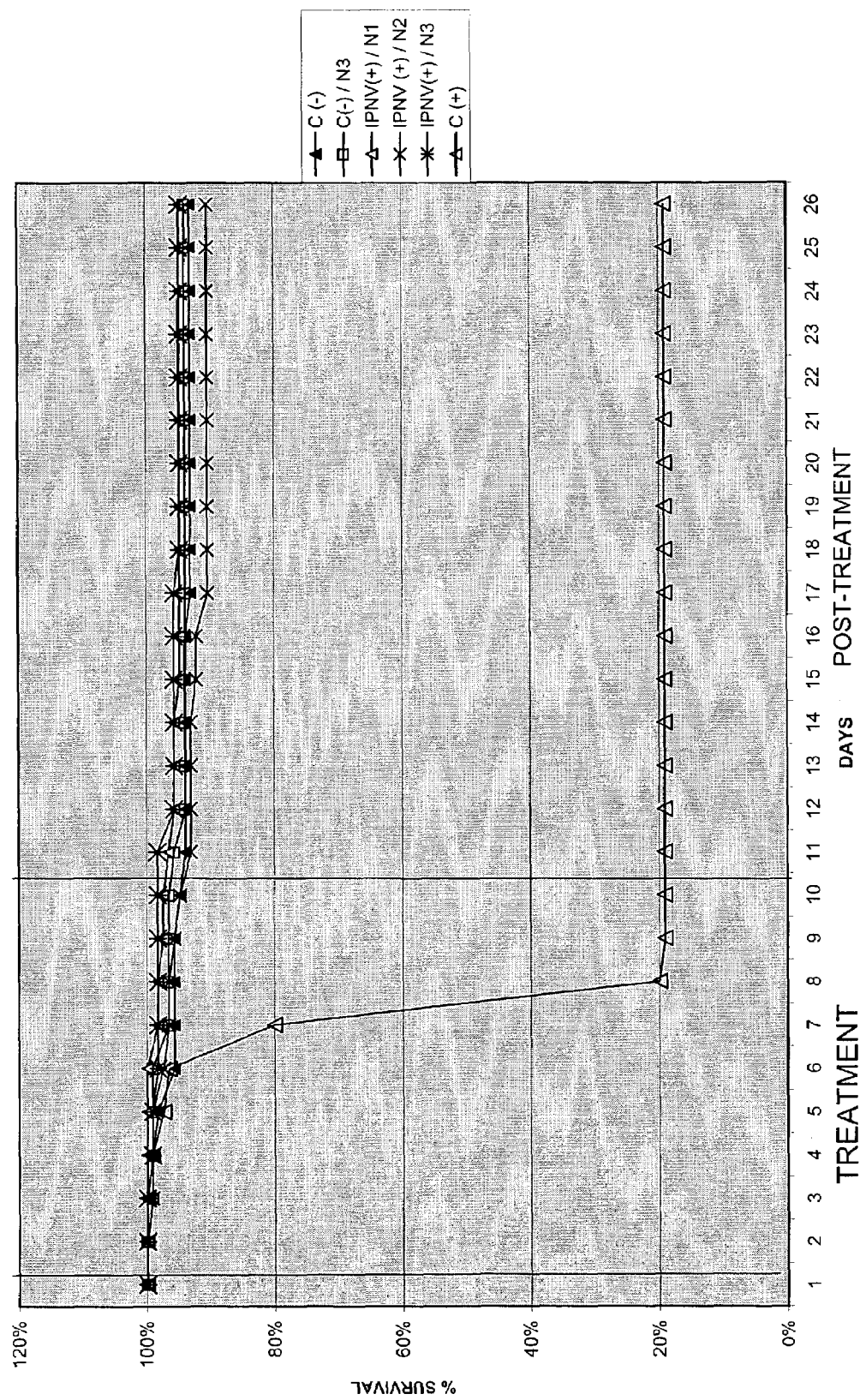

FIG. 7 is a graph showing the effect of various concentrations of neomycin treatments on the survival of Atlantic salmon fry following infection with IPNV. The salmon fry weighed about 0.45 to about 1.0 gms. On day 0, the fish are infected with $10^5$ pfu/ml of IPNV. One day post-infection, the fish are treated daily by immersion for 1 hour in a bath containing 10, 40 or 80 ppm of neomycin. Control uninfected fish fry are either treated daily for one hour with 0 or 80 ppm of neomycin. This daily treatment in neomycin continued through day 10 post-infection. The fish were followed for 26 days post-infection to document deaths. The data are presented graphically in terms of percent survival. Treatment of IPNV infected salmon fry at concentrations as low as 10 ppm can maintain survival to levels equivalent to the uninfected controls. The FIG. 7 legend indicates:

(▲-▲) Control (−)=negative control, non infected fish;

(◙-◙) Control (−)/N3=negative control, non infected fish treated with 80 ppm of neomycin at day 1 post-infection;

(Δ-Δ) Control (+)=positive control, untreated infected fish;

(X-X) IPNV(+)/N 1=infected fish treated with 10 ppm of neomycin at day one post-infection;

(x-x) IPNV(+)/N2=infected fish treated with 40 ppm of neomycin at day one post-infection; and (●-●) IPNV(+)/N3=infected fish treated with 80 ppm of neomycin at day one post-infection.

Figure 8:
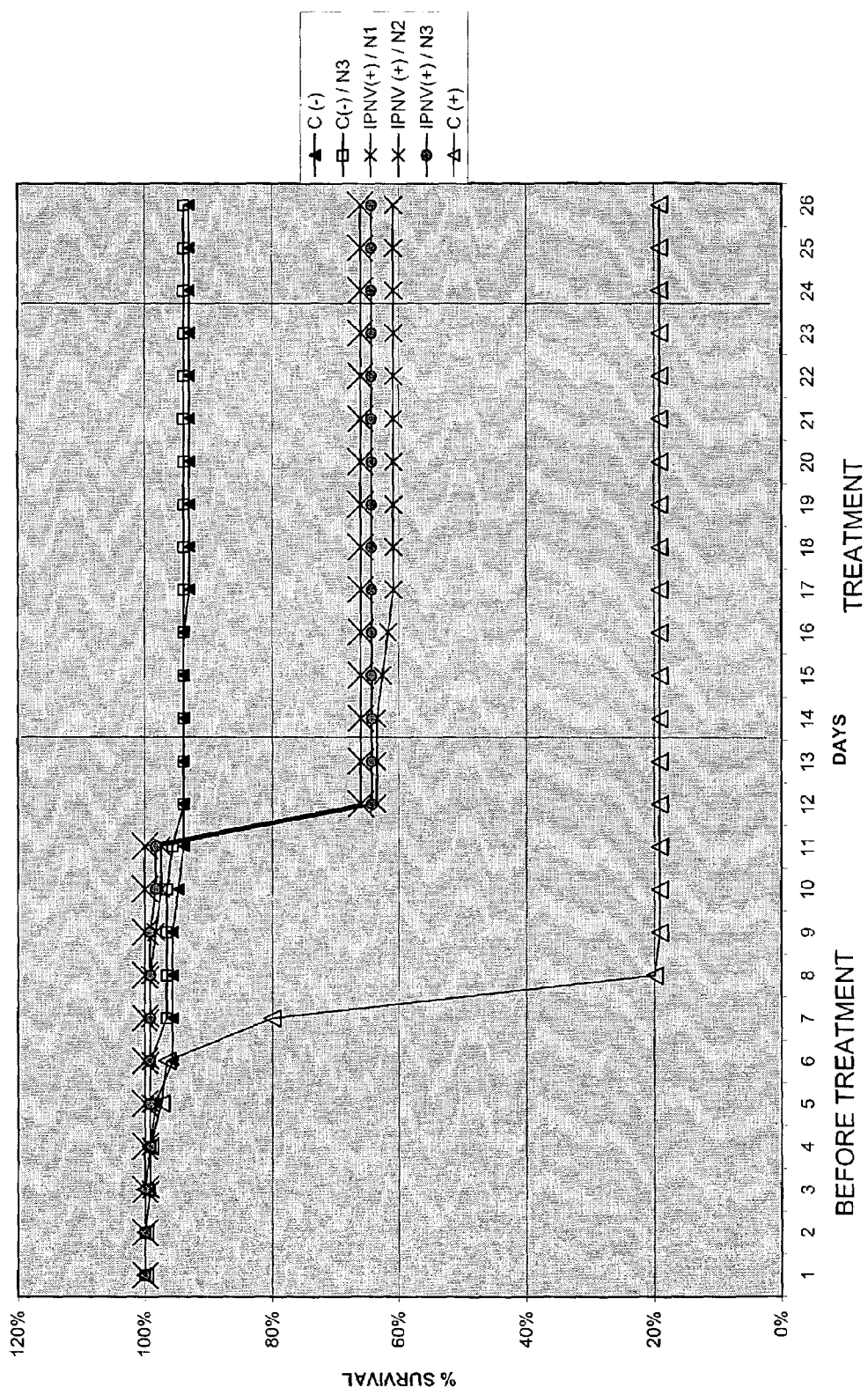

FIG. 8 is a graph showing the effect of various concentrations of neomycin treatments on the survival of Atlantic Salmon fry following infection with IPNV. The salmon fry weighed about 0.45 to about 1.0 gms. On day 0, the fish are infected with $10^5$ pfu/ml of IPNV. Starting thirteen days post-infection, after the mortality outbreak began, the fish are treated daily by immersion for 1 hour in a bath containing 10, 40 and 80 ppm of neomycin, and continued through day 23 post-infection. The fish were followed for 26 days post-infection to document deaths. The data are presented graphically in terms of percent survival. Neomycin treatment is able to stop the mortality outbreak immediately, avoiding increased of mortality. The FIG. 8 legend indicates:

Control (−)=negative control, non infected fish;

(◙-◙) Control (−)/N3=negative control, non infected fish treated with 80 ppm of neomycin at day 1 post-infection;

(Δ-Δ) Control (+)=positive control, untreated infected fish;

(X-X) IPNV(+)/N1=infected fish treated with 10 ppm of neomycin at day thirteen post-infection;

(x-x) IPNV(+)/N2=infected fish treated with 40 ppm of neomycin at day thirteen post-infection; and (●-●) IPNV(+)/N3=infected fish treated with 80 ppm of neomycin at day thirteen post-infection.

DETAILED DESCRIPTION OF THE INVENTION

The instant invention addresses a long standing need in aquaculture and animal production by providing a method of administering isoxazol and/or aminoglycoside compounds to aquatic and other animals susceptible to infection from a virus, particularly RNA viruses, selected from the group consisting of: IPNV, IBDV, pillar cell necrosis virus (PCNV), infectious hematopoietic necrosis virus (IHNV), viral hemorrhagic septicemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anemia virus (ISAV), tellina virus, oyster virus, a Birnaviridae virus, a Rhabdoviridae virus, an Iridoviridae virus, a Reoviridae virus, a Picornaviridae virus, and an Ortomixoviridae virus, in a manner that increases the survival of the animals. The term "animal(s)" includes living species in the animal kingdom, including aquatic animals and, therefore, is not limited to mammals.

The terms "administer" or "administered" or "administration" indicate any means by which the prophylactic/therapeutic compound is delivered to the animal so that the compound is available to block viral replication or entry. Such delivery means include, but are not limited to: introduction into the aquatic environment; inclusion in the food; and injection into the aquatic animal, such as intraperitoneal injection. Methods of administration also include: bathing the aquatic animals in tanks containing the compound; and inclusion of the compound in food. The method of the invention and the administering can be performed before, during, or after IPNV or IBDV exposure and/or infection. Further, the method can be conducted before, during, and/or after IPNV or IBDV infection as well as before, during and/or after IPNV or IBDV illness or death appears. For example, administration can be initiated after infection when 20% mortality is observed.

Administration includes those protocols that increase survival of an aquatic animal exposed to IPNV. Administration also includes those protocols that increase survival of an animal exposed to IBDV. Administration can occur before, during and/or after viral exposure. Such protocols include, but are not limited to the following: (a) inclusion of the antiviral compound in at least one daily feeding; (b) inclusion of the antiviral compound in the aquatic environment for at least 0.5-2.0 hours/day on a daily or cyclical schedule that includes, but is not limited to: biweekly, tri-weekly, and one-week-on/one-week-off; (c) administration prior to: the presence of viral titers, IPNV exposure, IPN illness, and/or IPNV-associated deaths; (d) administration upon detection of: the presence of viral titers, IPNV exposure, IPN-illness, and/or IPNV-associated deaths; (e) administration following: the presence of viral titers, IPNV exposure, IPN illness, and/or IPNV-associated deaths; (f) the protocols described herein; (g) daily administration for periods from about 5 days to about 30 days; and/or (h) administration for more than one time per day. Such protocols also include, but are not limited to the following: (a) administration prior to: the presence of viral titers, IBDV exposure, IBDV illness, and/or IBDV-associated deaths; (b) administration upon detection of: the presence of viral titers, IBDV exposure, IBDV-illness, and/or IBDV-associated deaths; (c) administration following: the presence of viral titers, IBDV exposure, IBDV illness, and/or IBDV-associated deaths; (d) the protocols described herein; and/or (g) daily administration for periods from about 5 days to about 30 days.

The stability of the compound to be used in the present methods and compositions, including food compositions, is determined and is accounted for in the method of administering the composition containing the compound and in the mode of preparing the composition containing the compound. In fish cultivation centers and animal farms, it is important to have a method of treatment that can be used before, during, and/or after IPNV or IBDV infection, as well as before, during and/or after IPNV or IBDV illness or death appears. Stability in solution, dry food compositions and/or moist or wet food compositions is one characteristic of the preferred compounds employed in the method and compositions of the invention.

"Therapeutic effective amount" or "effective amount" is that amount of the compound, such as an isoxazol compound or aminoglycoside compound, that is sufficient to increase survival by from about 10 to about 70 percent. Preferably, the effective amount is that which reduces the viral load in the animal, or reduces the average viral load in the population being treated. Preferably, the effective amount is not toxic to more than about 5% to about 10% of the treated aquatic or other animals. Those of skill in the art can determine the concentrations of the compound, such as an isoxazol compound or an aminoglycoside compound, that are therapeutically. Such concentrations can vary with the method of administration and the compound. For instance, to administer the isoxazol compounds or aminoglycoside compounds by bathing the fish in water, the compound concentrations in the water range from about 1-50 μg/ml, preferably about 2-20 μg/ml, more preferably about 6-14 μg/ml. The therapeutic effective amount delivered as a component of fish food is about 0.1-10.0 μg isoxazol compound/gram of food. The therapeutic effective amount delivered by direct injection is calculated after injection of about 2-20 μg isoxazol compound per gram of fish mass, and identifying the dose at which survival upon exposure to IPNV increases at least 10% above controls. For guidance as to the initial concentrations to be tested, the $EC_{50}$ and $CC_{50}$, of the specific isoxazol compound are determined, and the mass of the aquatic animal to be treated is determined. The therapeutic effective amount of neomycin for antiviral activity by immersion/bathing the fish in water, for example, is from about 5 to about 110 ppm, preferably from about 40 to about 80 ppm. The therapeutic effective amount of neomycin for increasing the survival of virally infected aquatic animals is from about 20 to about 50 mg/kg for oral dosing, preferably from about 25 to about 40 mg/kg. The therapeutic effective amount of injected neomycin for increasing the survival of virally infected aquatic animals is from about 4 mg/kg to about 6 mg/kg. A preferred treatment period for immersion is about 3 days; a preferred treatment period for oral dosing is about 5 days; a preferred injection treatment protocol is one administration. Of course, application methods can be combined; for example, immersion treatment can be combined with oral treatment of isoxazol compounds and/or aminoglycoside compounds.

As used herein, the term "viral load" means that concentration of virus present in an organism and is expressed in terms of plaque forming units. Plaque forming units can be determined several ways. One way to determine the concentration of virus is as follows: A tissue sample is obtain and assayed on monolayers of Chinook salmon embryo cell line (CHSE-214)grown at 18° C. in Minimum Essential Eagle Medium (MEM), supplemented by 5% fetal bovine serum (FBS) and antibiotics to a confluence of about 90%. After one hour, the cells are overlaid with 0.5% agarose in MEM supplemented with 10% FBS and incubated for 3 days at 15° C. At various times, the cells are fixed with formaldehyde and stained with a 0.5% crystal violet solution to detect lysed cells. The number of plaques formed is counted and divided by the amount of sample provided to arrive at the number of plaque forming units (pfu) per ml. Viral load can also be approximated by correlation with the appearance of certain symptoms in the aquatic animals. For example, the titer range for a fish that has tissue damage and lesions can be in the range of about $10^5$ to $10^9$ pfu/ml.

The presence, viral titer, and viral load of an aquatic virus, such as IPNV, IBDV, PCNV, IHNV, VHSV, or another specific Birnaviridae virus, Rhabdoviridae virus, Iridoviridae virus, Reoviridae virus, Picomaviridae or Orthomixoviridae virus can be determined. The virus is identified and/or quantified from tissue samples taken from the aquatic animal, or by observing the various clinical traits and behaviors associated with the specific virus. Methods for measuring the viral titer are known in the art and discussed elsewhere herein.

Aquatic birnavirus/IPNV is classified and/or identified based on seroneutralization assays, cell culture assays, reverse transcriptase polymerase chain reaction (RT-PCR) assays, restriction enzyme analysis and/or sequence analysis. The RT-PCR assay is the most a rapid, specific, and sensitive method to detect and identify aquatic birnaviruses. There are at least 9 type strains of Serogroup A and 4 other representative strains of Serotype A1 of IPNV, which is the predominant aquatic birnavirus and IPNV serotype in the United States. Primer sequences that are highly conserved among aquatic birnaviruses are used in PCR assays to identify all recognized serotypes of aquatic birnavirus serogroup A. Primers are typically specific for regions of cDNA coded by genome segment A or the entire VP2 coding region of aquatic birnaviruses.

IBDV and its strains/variants are characterized and/or identified using immunoassays, such as an Enzyme-linked immunoabsorbent assay (ELISA) and/or a molecular assays such as the quantitative reverse transcriptase polymerase chain reaction (RT-PCR) and the RT-PCR restriction fragment length polymorphism (RT/PCR-RFLP). See, Kreider D L, et al., Avian Dis 35:276-87 (1991); Moody, A. et al., J Virol Methods, 85:55-64 (2000); Jackwood D J, et al., Avian Dis 45:330-9 (2001),the contents of which are hereby incorporated by reference in their entirety. Differentiation of IBDV strains is important because differences exist in their ability to cause disease and their antigenic types. The molecular assay is used to differentiate viruses into genetically-related groups called molecular groups. There are six molecular groups observed for vaccine and laboratory strains of IBDV; strains within a group are antigenically related.

Aquatic birnavirus or IPN viral titer or viral load is determined by identifying and/or quantifying the presence of IPNV in tissue samples taken from aquatic animals, or through observation of various clinical traits and behaviors. Methods for IPNV detection, identification and quantification (measuring IPNV viral titer) are known in the art and include the reverse transcription polymerase chain reaction (RT-PCR) method conducted on tissue samples from the kidney and spleen of the analyzed fish according methods known in the art. See, for example, López-Lastra et al, J. Fish Dis. 17: 269 (1994), the contents of which are hereby incorporated by reference in their entirety.

Similarly, IBDV viral titer or viral load is determined by identifying and/quantifying the presence of IBDV in tissue samples taken from birds, or through observation of various clinical traits and behaviors. Methods for IBDV detection, identification and quantification (measuring IBDV viral titer) are known in the art and include the ELISA, quantitative RT-PCR and RT-PCR-RFLP assays discussed above, and according to methods known in the art.

Kidney, liver, spleen and/or ovarian fluid samples are obtained from asymptomatic fish, such as bloodfish, at spawning time. Samples from a clinically affected fish, such as whole alevin, entire viscera, kidney, liver and/or spleen are tested for the presence and quantity of IPNV.

The terms "treating" and "treat" as used herein mean "administering" as defined herein and also includes eliminating or reducing the symptoms of a disease or disorder, preventing the symptoms or disorder from increasing in severity, and preventing the disorder form occurring.

A compound is "stable in solution" when it (a) does not easily decompose or otherwise modify chemically in solution in a manner that renders it non-functional and/or (b) maintains its intended activity when wet or in solution for a period of time greater than 1 hour, preferably for 24 hours, most preferably for periods of weeks or greater.

The compounds to be used in accordance with the present invention include: isoxazol compounds and aminoglycosides. Many isoxazol compounds are available publicly from such sources as Sigma-Adrich, Sterling Winthrop, Inc., and Sanofi Winthrop, Inc. The following is a partial listing of representative species of isoxazol compounds that can be used in the present invention.

The term "isoxazol compound" means a compound containing the Formula

These compounds are generally known in the art. For example, see U.S. Pat. Nos. 4,208,510; 4,843,087; 4,942,241; 4,945,164; Re 21,578; 5,464,848; and 6,174,909, the contents of each of which are hereby incorporated by reference in their entirety.

The preferred isoxazol compounds are acivicin and the isoxazol derivatives known as WIN compounds. One such isoxazol compound, acivicin, is stable in solution.

The preferred isoxazol derivatives known as WIN compounds, are isoxazole-derived drugs developed by Sterling-Winthrop, many of which are known to bind in a hydrophobic pocket within the virion capsid protein. Members of the WIN compound family are well known in the art. For example, see U.S. Pat. Nos. 5,464,848; 5,643,929; and 4,857,539; and Vaidehi et al., PNAS USA 94:2466 (1997), the contents of each of which are hereby incorporated by reference in their entirety. WIN compounds include 1,2,4-oxadiazolyl-phenoxyalkylisoxazoles compounds.

One group of preferred isoxazol compounds, the acivicin compounds and analogues, are compounds having an isoxazol ring with $R_1$ at position 1, R2 at position 2, and R3 at position 3, wherein $R_1$ is selected from the group consisting of a straight- or branched-chain alkyl, alkenyl or alkynyl having up to 6 carbon atoms, optionally substituted by one or more halogens or cycloalkyl having from 3 to 6 carbon atoms, optionally bearing one or more substituents, cycloalkenyl having 5 or 6 carbon atoms, optionally bearing one or more substituents selected an aryl or aralkyl group; R2 is selected from the group consisting of nitro, cyano, halogen, hydrogen or straight- or branched-chain alkyl having up to 6 carbon atoms, optionally substituted by one or more halogens; R3 is selected from the group consisting of a straight- or branched-chain alkyl having up to 6 carbon atoms, optionally substituted by one or more halogens.

Acivicin is also named L (alpha S, 5S) alpha-amino-3-chloro-4.5-dihydro-5-isoxazolacetic acid or (αS, 5S)-α-amino-3-chloro-2-isoxazoline-5-acetic acid or AT-125. Acivicin and its analogues are described in U.S. Pat. Nos. 3,856,807; and 3,878,047. The contents of U.S. Pat. Nos. 3,856,807 and 3,878,047 are hereby incorporated by reference in their entirety.

Methods of purifying acivicin are described in U.S. Pat. Nos. 4,188,324; 4,225,720; and 4,232,164. A chemical process for synthesizing acivicin and its analogues, such as the alpha substituted amino-3-substituted-2-isoxazoline-5-acetic acids (esters) is described in U.S. Pat. No. 4,256,898 and RE31,578, the entirety of each of which are hereby incorporated by reference. It involves preparing the compound dl-trans-3-amino-4-hydroxy-cyclopentene, which is converted by a series of reactions to yield the tricholomic acid derivatives, acivicin and bromo, fluoro and iodo analogues thereof.

The preferred isoxazol compounds used in the method and compositions of the present invention are:

(A) Acivicin (also referred to as L (alpha S, 5S) alpha-amino-3-chloro-4,5-dihydro-5-isoxazolacetic acid; (αS,5S)-α-amino-3-chloro-2-isoxazoline-5-acetic acid; or AT-125) and its analogues. The acivicin compounds and analogues employed in the instant method and compositions, including food compositions, are racemic mixtures and optically active isomers of compounds having the Formula

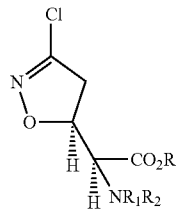

wherein R is selected from the group consisting of hydrogen and alkyl of from 1 to 8 carbon atoms; $R_1$ and $R_2$ are different and are selected from the group consisting of hydrogen, a compound having the Formula

or when taken together with the nitrogen atom form the group having the Formula

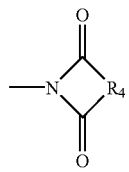

wherein R3 is alkyl of from 1 to 8 carbon atoms, inclusive; and R4 is selected from the group consisting of (a) a compound having the Formula

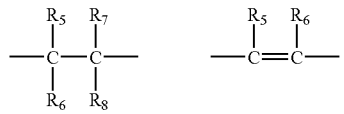

wherein $R_5$, $R_6$, $R_7$ and $R_8$ are selected from the group consisting of hydrogen and alkyl of from 1 to 5 carbon atoms, inclusive (b) a compound having the Formula

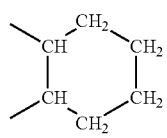

(c) orthointerphenylene, and (d) substituted orthointerphenylenes with the proviso that other than when $R_1$ and $R_2$ form a ring with the nitrogen atom one of $R_1$ and $R_2$ must always be hydrogen, preferably R and $R_1$ are hydrogen and $R_2$ is alkoxycarbonyl; most preferably $R_2$ is L-butyloxycarbonyl and the compound is 3-chloro-2-[[(1,1-dimethoxy)carbonyl]amino[-4,5-dihydro-5-isoxazoleacetic acid; also preferably R is hydrogen and $R_1$ and $R_2$ together with the nitrogen atom form the group having the Formula

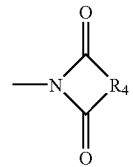

more preferably $R_4$ is orthointerphenylene and the compound is phthalyl-(αS,5S)-α-amino-3-chloro-4,5-dihydro-5-isoxazolacetic acid; as well as racemic mixtures and optically active isomers of compounds having the Formula

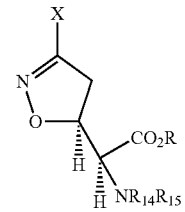

wherein R is selected from the group consisting of hydrogen, alkyl of from 1 to 8 carbon atoms, inclusive, halogenated alkyl of from 1 to 3 halogen atoms, and 1 to 5 carbon atoms, inclusive, aralkyl of from 7 to 20 carbon atoms, inclusive; and substituted aralkyl of from 7 to 20 carbon atoms, inclusive. X is selected from the group consisting of bromine, chlorine, fluorine and iodine, $-OR_1$, $-SR_1$, and $-NR'R''$ wherein $R_1$ is selected from the group consisting of alkyl of from 1 to 12 carbon atoms, inclusive, aryl of from 6 to 20 carbon atoms, inclusive; aralkyl of from 7 to 20 carbon atoms; inclusive; R' and R'' are the same or different and are selected from the group consisting of hydrogen and alkyl of from 1 to 8 carbon atoms; $R_{14}$ and $R_{15}$ are selected from the group consisting of hydrogen, a compound having the Formula

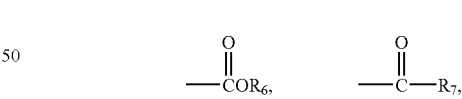

or when taken together with the nitrogen atom or the group having the Formula

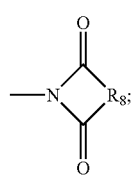

wherein $R_6$ is alkyl of from 1 to 8 carbon atoms, inclusive, halogenated alkyl of from 1 to 5 carbon atoms, inclusive, and 1 to 3 halogen atoms, inclusive, aralkyl of from 7 to 20 carbon atoms, inclusive, and substituted aralkyl of from 7 to 20 carbon atoms, inclusive, $R_7$ is selected from the group consisting of alkyl of from 1 to 12 carbon atoms, inclusive, aryl of from 6 to 20 carbon atoms, inclusive, aralkyl of from 7 to 20 carbon atoms, inclusive, and substituted aralkyl of from 7 to 20 carbon atoms, inclusive; and $R_8$ is selected from the group consisting of a compound having the Formula

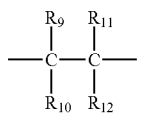

wherein $R_9$, $R_{10}$, $R_{11}$ and $R_{12}$ are selected from the group consisting of hydrogen and alkyl of from 1 to 5 carbon atoms, inclusive, (b) a compound having the Formula

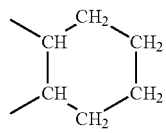

(c) an orthointerphenylene compound having the Formula

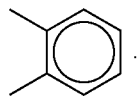

and (d) substituted orthointerphenylene with the proviso that when R, $R_{14}$ and $R_{15}$ are all hydrogen, X cannot be chlorine, and the further proviso that when $R_{14}$ and $R_{15}$ are both hydrogen and $R_8$ is orthointerphenylene, R can not be hydrogen or alkyl of from 1 to 8 carbon atoms; (B) a WIN compound of the Formula

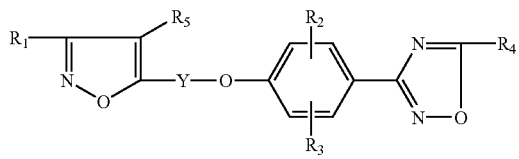

wherein: $R_1$ is alkyl, alkoxy, hydroxy, cycloalkyl, hydroxyalkyl, alkoxyalkyl, hydroxyalkoxy, alkylthioalkyl, alkylsulfinylalkyl, alkylsulfonylalkyl, aminoalkyl, alkylaminoalkyl, dialkylaminoalkyl, alkoxycarbonyl, carboxy, or cyanomethyl; Y is alkylene of 3 to 9 carbon atoms, $R_2$ and $R_3$ independently are hydrogen, alkyl, alkoxy, halo, cyano, trifluoromethyl and nitro; $R_4$ is alkoxy, hydroxy, halomethyl, dihalomethyl, trihalomethyl, dihaloethyl, cycloalkyl, heterocyclyl, alkoxycarbonyl, hydroxyalkyl, alkoxyalkyl, alkanecarbonyloxyalkyl, cyano, halo, thioalkyl, alkylthioalkyl, alkylthio, thio, 2,2,2-trifluoro-ethyl, (4-methylphenyl) sulfonyloxymethyl, N=Q or CON=Q, wherein N=Q is amino, alkylamino or dialkylamino; $R_5$ is hydrogen or halo or alkyl; (C) WIN compounds identified in U.S. Pat. No. 4,857,539, the contents of which are incorporated by reference in their entirely, such WIN compounds have the Formula

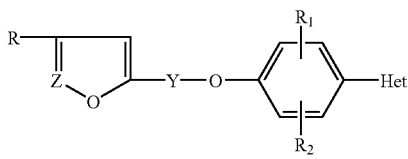

wherein: Y is an alkylene bridge of 3-9 carbon atoms; Z is N; R is hydrogen or lower-alkyl of 1-5 carbon atoms, with the proviso that when Z is N, R is lower-alkyl; $R_1$ and $R_2$ are hydrogen, halogen, lower-alkyl, lower-alkoxy, nitro, lower-alkoxycarbonyl or trifluoromethyl; and Het is selected from specified heterocyclic groups, unsubstituted 1,3,4 oxadiazol-2-yl and unsubstituted 1,2,4-oxadiazol-5-yl. In the WIN compounds, when the 1,2,4-oxadiazole ring is substituted by hydroxy, amino or alkylamino, they may exist in tautomeric forms wherein $R_4$ is hydroxy, amino or alkylamino and T is O, NH or N-alkyl.

Additional compounds to be used in accordance with the present invention are aminoglycosides. Such aminoglycosides include, but are not limited to, the following: neomycins (for example neomycin B), paramomycin, streptomycin, tobramycin (for example tobramycin or dibekacin), kanamycin, (for example mixtures of kanamycin A, B and C), amicacin, gentamycin, (for example mixtures of gentamycin A, C1, C2 or C1a), sisomycin (such as sisomycin or netilmycin), lividomycin, and ribocamycin.

Additional compounds to be used in accordance with the present invention include, but are not limited to the following:

adenine analogues, including (S)-9-(2.3-dihydroxypropyl) adenine (DHPA) and 3-adenine-9-yl-2-hydroxypropanoic acid (AHPA);

3'-fluoro guanosine and 9-(2-hydroxy ethoxymethyl) guanine (acyclovir);

Pirazofurine;

Plant extracts, such as *Durvillea antartica;* and

Mycophenolic acid.

As used herein, unless otherwise specifically defined, alkyl, alkane, alkoxy, cycloalkyl and halo each has the following meaning: alkyl and alkoxy mean aliphatic radicals, including branched radicals, have from one to five carbon atoms. The alkyl moiety of such radicals include, for example methyl, ethyl, propyl, isopropyl, n-butyl, sec-butyl, t-butyl and pentyl. "Alkane" means a monovalent aliphatic alkyl radical, including branched radicals of from one to four carbon atoms. Thus, the alkane moiety of such radical includes, for example, methyl, ethyl, propyl, isopropyl, n-butyl and sec-butyl. Cycloalkyl means an alicyclic radical having from three to six carbon atoms, as illustrated by cyclopropyl, cyclobutyl, cyclopentyl and cyclohexyl. Heterocyclyl refers to a 5 or 6 membered carbon based heterocycle, having from one to about three nitrogen atoms and/or one oxygen or sulfur atom, provided that no two oxygen and/or sulfur atoms are adjacent in the heterocycle. Examples include furyl, thienyl, pyridyl, oxadiazolyl, thiadiazolyl, triazinyl, pyrimidinyl and the like.

As used herein, in hydroxyalkyl and alkoxyalkyl, the hydroxy and alkoxy groups can occur at any available position of alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2, 3, 4 and 5-hydroxy-pentyl and the like and corresponding alkyl ethers thereof.

As used herein, in hydroxyalkoxy, the hydroxy group can occur at any available position of alkoxy other than the C-1 position. Thus hydroxyalkoxy includes, for example, 2-hydroxyethoxy, 2-hydroxypropoxy, 2-hydroxyisopropoxy, 2 and 5-hydroxypentoxy and the like.

"Lower-alkyl" means methyl, ethyl, propyl, butyl, pentyl, hexyl, heptyl, octyl and the isomeric forms thereof.

"Halogenated alkyl of from 1 to 5 carbon atoms, inclusive, and 1 to 3 carbon atoms, inclusive," means methyl, ethyl, propyl, butyl, pentyl and isomeric forms thereof substituted by 1 to 3 halogen atoms.

"Aryl" means phenyl and phenyl containing 1 to 3 substituents, the same or different and selected from the group consisting of halogen, alkoxy, alkyl and nitro.

"Aralkyl" means benzyl, phenethyl, phenpropyl, phenbutyl, phenpentyl, diphenylmethyl, three diphenyloctyl and isomeric forms thereof and fluorenylmethyl.

"Substituted aralkyl" means aralkyl in which the phenyl ring or rings contain 1 to 3 substituents, the same or different, and selected from the group consisting of halogen, alkoxy, alkyl and nitro. This includes, for example, p-methoxybenzyl, m-methoxybenzyl, p-nitrobenzyl, o-chlorobenzyl, 4-propyl-2-methylbenzyl, 2-chloro-4-methylbenzyl, 3,4-diethoxybenzyl, 3,4-diethoxybenzyl, 3,4,5-trichlorobenzyl and 3,4,5-trimethylbenzyl.

"Substituted orthointerphenlene" means lower-alkyl, lower-alkoxy, halogen, nitro, and cyano-substituted orthointerphenylene. There can be combinations of substituents such as 4-propyl-2-methyl-, 2-chloro-4-methyl-, 3,4-diethoxy-, 3-cyano-4-ethoxy-phenyl and the like. The substituted phenyl is limited to a total of 10 carbon atoms.

"Halogen" means bromine, chlorine, fluorine and iodine. "Halo" means bromo, chloro, iodo or fluoro.

As used herein, the term "aquatic animal susceptible to infection with a virus" is intended to mean that any one of the following viruses: IPNV, pillar cell necrosis virus (PCNV), infectious hematopoietic necrosis virus (IHNV), viral hemorrhagic septicemia virus (VHSV), infectious hypodermal and hematopoietic necrosis virus (IHHNV), shrimp white spot virus (WSV), Taura syndrome virus (TSV), hepatopancreatic parvovirus (HPV), infectious salmon anemia virus (ISAV), tellina virus, oyster virus, a Biruaviridae virus, a Rhabdoviridae virus, an Iridoviridae virus, a Reoviridae virus, a Picomaviridae virus, and an Ortomixoviridae virus is capable of replicating in and/or residing in the aquatic animal in a manner that it can be detected in a tissue of the aquatic animal. Such infection may be asymptomatic and may be transmitted to other aquatic animals horizontally and/or vertically.

As used herein, the term "aquatic animal susceptible to aquatic birnavirus infection" is intended to mean that an aquatic biruavirus or IPNV is capable of replicating in and/or residing in the aquatic animal in a manner that it can be detected in a tissue of the aquatic animal. Such infection may be asymptomatic and may be transmitted to other aquatic animals horizontally and/or vertically.

The term "aquatic biruavirus" is intended to encompass any Birnavirus that infects an aquatic organism. The preferred aquatic birnavirus is the IPNV, which is known to include at least nine serotypes.

The term "aquatic animal" includes, but is not limited to fish, copepods, cephalopods, crustaceans including shrimp, eels, and mollusks, including oysters. The preferred aquatic animals are fish, which include but are not limited to fish from the families Anguillidae, Bothidae, Caragidae, Cotostomidae, Chichlidae, Clupeidae, Cobitidae, Coregonidae, Cyprinidae, Esocidae, Moronidae, Paraichthydae, Percidae, Poecilidae, Salmonidae, Salvelinus, Sciaenidae, Thymallidae and the species *Seriola quinqueradiata* (yellowtail), *Scophthalmus maximus* (turbot), *Limanda limanda* (dab), *Hippoglossus hippoglossus* (halibut), *Gadus morhua* (Atlantic Cod), *Misgrunus anguillisaudatus* (loach), and *Esox lucious* (pike). The most preferred fish are those listed in Table 1. The most preferred shellfish/crustaceans are listed in Table 1 as well. The term "salmonoid" is used herein to refer to fish of the families Salmonidae and Salvelinus. In addition to all trouts, these families include, but are not limited to, the following salmon species: *Oncorhynchus tshawytscha* (Chinook, King, or Spring), *Oncorhynchus nerka* (Blueback, Red, Sockeye), *Oncorhynchus kisutch* (Coho, Silver), *Oncorhynchus gorbuscha* (Pink), *Onchorhynchus mykiss* (Rainbow trout ), *Oncorhynchus keta* (Chum, or Keta), and *Oncorhynchus masou* (Masou, or Cherry).

A comparison of the sequence of the IPNV viral protease VP4 with the VP4 of infectious bursal disease virus (IBDV), suggests that they are similar serine proteases that share properties with prokaryotic peptidases and bacterial peptidases. Compounds within the scope of the instant invention that inhibit the VP4 of IPNV may also be effective in inhibiting the IBDV viral protease VP4. Therefore, compositions of the instant invention for treating IPNV infection can be used in methods of the instant invention for increasing the survival of animals susceptible to IBDV. The instant invention is also directed, therefore, to methods and compositions for the treatment of infectious bursal disease virus (IBDV) in birds, particularly chickens, to increase the survival of birds exposed to IBDV.

For administration, the composition employed in the method of the instant invention can be prepared either by processing the isoxazol or isoxazol derivative into a dosage form such as a powder, dust, microfine granule, granule, fine granule, tablet, liquid, pellet or syrup with or without a solid, semi-solid or liquid vehicle or by supplementing fish food with the compound or the dosage form. The vehicle may include raw fish mince (e.g., minced mackerel, sardine, sand lance, saury, Alaska Pollock, squid, etc.), formulated feed (based on fishmeal, soybean cake, yeast, wheat flour, vitamins, etc.,) and such other conventional vehicles as lactose, sucrose, glucose, starch, talc, acid clay and so on. In addition, emulsifiers, dispersants, gelling agents, adhesives, etc. may be added in appropriate proportions.

Such compositions containing the compound can be administered to prevent and/or treat virus infections in aquatic animals susceptible to virus infection. Also, such compositions containing the compound can be administered for the prevention and/or treatment of IPNV infection in aquatic animals susceptible to IPNV infection. For the prophylaxis or treatment of IPNV in salmon or trout, for instance, one preferred treatment modality comprises, taking advantage of the stability of the compound in raw fish mince, adding a powdery or fine granular premix of the compound with the vehicle to a raw fish mince, or a mixture of such raw fish mince and formulated feed and administering the whole mixture either as it is or as premolded into pellets or moist pellets.

The dosage and duration of administration of the present prophylactic/therapeutic composition for treating aquatic animals susceptible to virus infection, including IPNV infection, are dependent on the specific isoxazol compound, species, age, water temperature, severity of disease, etc. For the prevention and therapy of IPNV in salmon or yellowtail, for instance, generally 20-50 μg of acivicin can be administered orally per day per gram fish body weight, daily.

In one preferred embodiment, the prophylactic/therapeutic composition of the present invention contains an isoxazol or isoxazol derivative compound that: (1) increases aquatic animal survival in the presence of IPNV; and (2) is stable in fish food, such as raw fish mince. The composition administered to fish after being mixed with a raw fish mince, is one that insures a high concentration of isoxazol in fish blood over a protracted period of time Although inhibitors of IPNV replication in vitro may not prove to have in vivo efficacy, the in vitro assays can be used to identify compounds that exhibit antiviral activity and/or lower cytotoxicity, before determining and in vivo efficacy and safety.

Methods for identifying compounds that block viral replication in vitro are known in the art. Jashes et al. Antiviral Res. 29:309 (1996). To determine if a compound is capable of blocking IPNV replication in vitro, monolayers of Chinook salmon embryo cell line (CHSE-214) are grown at 18° C. in a minimum essential Eagle medium (MEM), supplemented by 5% fetal bovine serum (FBS) and antibiotics to a confluence of about 90 percent. The monolayers infected with 50-100 plaque forming units (pfu) of an IPNV strain, such as strain VR-299a. After absorption for one hour with agitation every 15 minutes, a sample of the virus is withdrawn. The cells are overlaid with 0.5% agarose in MEM supplemented with 10% FBS and allowed to incubate for 3 days at 15° C. The tested compound is added at several different concentrations in the agarose overlay. At various timepoints during and after incubation, the cells are fixed with formaldehyde and stained with a solution of 0.5% crystal violet to detect cells that have lysed. By comparing the number of plaques formed at various concentration of the assayed compounds, the 50% ($EC_{50}$) and by 100% ($EC_{100}$) are determined. Assays are repeated at least three times to determine variability and to obtain accurate results.

General methods that measure a compound's cytotoxic effect in vitro are known, such as those described by Jashes et al., supra (1996). In one such method, different concentrations of the compound are added to monolayers of CHSE-214 cells. Cell monolayers are incubated with the compound at 15° C. for three days. Cell viability is measured by cell exclusion of trypan blue. The cytotoxic concentration required to reduce cell viability by 50% ($CC_{50}$) is determined.

Methods for measuring compounds that block cellular DNA synthesis in vitro are known in the art, such as those described in Jashes et al., supra (1996). In one such method, CHSE-214 cells were grown to approximately 50% confluence to insure active growth occurs. Different concentrations of the compounds are added to the cells along with 1.0 μCi/ml [methyl $^3$H] thymidine (having a specific activity of about 67 Ci/mmol) and incubated for 20 hours at 15° C. The incorporated $^3$H-thymidine is measured as that radioactivity associated with the acid insoluble material. The concentrations of the compound that is required to reduce [methyl $^3$H] thymidine incorporation by 50% ($IC_{50}$) is determined to identify a compound and its concentration that blocks DNA synthesis.

The fish were acclimated for one week, during which time random water and tissue samples are collected and tested for the presence of bacteria and viruses. Samples are submitted to cultures in tryptone soy agar (TSA), kidney disease medium (KDM-2), and CHSE-214 cell cultures with and without antibiotics.

The SP strain of IPNV is propagated in Chinook salmon embryo cells (CHSE-214), and can be titrated and stored at −70° C. for future use. Acivicin (L (alpha S, 5S ) alpha-amino-3-chloro-4.5-dihydro-5-isoxazolacetic acid) was obtained from Sigma. Fish can be obtained from innumerable sources. For some of the examples in the instant invention, some of the fish used were obtained from the University of Chile located in Chiloé Island.

The Atlantic salmon fry employed in the examples are typically 90 days old and weight 1 ±0.2 g. The fry are distributed into groups of 50 each and held in 10-12° C. water. 80% of the water is changed daily; every five days the water is changed completely. The fish fed twice daily with quantities of food that are 3% of their body weight. The fry are observed and clinical symptoms, deaths and/or abnormal behavioral characteristics are carefully recorded.

Fish infected experimentally are exposed to a virus by being placed in 10-12° C. water containing approximately $10^4$ pfu/ml of the virus, such as IPNV strain Sp, for 2 hours. Exposure to the virus typically coincides with feeding in order to facilitate the uptake of IPNV. Uninfected control groups are treated using the same methods as those of the infected groups, except cell culture medium is added instead of a virus.

The antiviral agents can be administered by exposing the fish to the antiviral agent for the time period and protocol specified. One range of concentration of the isoxazol compounds administered is 0.1 to 100 μg/ml. Preferably, the isoxazol compound concentrations are 1-20 μg/ml when acivicin is used; more preferably the acivicin concentrations are 9-14 μg/ml or greater.

The instant method and composition can be applied to aquatic animals of all ages, to lower mortality and thereby increase yields. Lower mortality and increased yields also can be achieved for fish that remain as viral carriers.

For administration of an isoxazol compound, the concentration(s) that reduces the incorporation of [methyl-$^3$H] thymidine by 50% ($IC_{50}$) is used as an initial indication of the concentration or dose range to be initially assessed before identification of the therapeutic effective amount. For example, less than 25 μg/ml acivicin is the $IC_{50}$ for IPNV. Fry are immersed for 2 hours in a solution containing 7 μg/ml, 10.5 μg/ml, or 14.0 μg/ml of acivicin. Uninfected fry undergo the same stress handling in the absence of the antiviral compound. This administration is tested before, during, and after IPNV exposure and/or infection. For example, the acivicin can be administered after infection when 20% mortality is observed, and on subsequent days at least one-per-day. In fish cultivation centers, it is important to have a treatment method that can be initiated before, during, and/or after IPNV infection as well as before, during and/or after IPN illness or death appears. The stability of the compound to be used in the present methods and food compositions is another important characteristic that effects the method and mode of preparation and administration of the compound. Many of the compounds used in the instant method and compositions are stable in solution. For example, acivicin is stable in solution.

IPNV detection, identification and quantification is carried out using the reverse transcription polymerase chain reaction (RT-PCR) with tissue samples (e.g., kidney and spleen) from the fish or other aquatic animal using methods known in the art, such as that disclosed in López-Lastra et al, J. Fish Dis. 17: 269 (1994), the entirety of which is incorporated by reference herein in its entirety. The first amplification is done with such primers as primers III and IV, which obtain a 657 bp product. In the second amplification, such primers as I and II are used, which obtain a 228 bp product. The PCR products are visualized by silver staining, after being rune electrophoretically on a 12% polyacrylamide gel (PAGE).

Administration of the method and composition of the instant invention not only increases the yield of the treated fish, but also can lower the viral titers present in the surviving IPNV-infected aquatic animal carriers. The instant method of treating IPNV infections in fish may be a preferred means for increasing salmon and trout production and yields.

Transmission of IPNV is both horizontal and vertical. For select breeders that may prefer to utilize virus-free stocks to breed their aquatic animals (such as salmon and trout), the preferred compounds to be used in the method and compositions of the instant invention are those that are capable of eliminating IPNV in the breeding stocks. Such elimination of IPNV titer is documented using the virus detection methods described elsewhere herein.

The preferred compounds are screened for their ability to diminish and/or eliminate infective viral progeny and their ability to inhibit viral replication in vivo is determined. Also, the inhibitory effect of the compound on the formation of viral particles is determined. Further, the viral samples are exposed to the compound overnight and their titers are assessed thereafter. Those compounds that lower the viral titer by an order of magnitude lower indicate the ability of the compound to effectively diminish infective viral progeny. The ability of the compound to diminish and/or eliminate infective viral progeny in vivo and/or inhibit viral replication in vivo is determined by methods known in the art, which include the assessment of the compound's ability to increase the survival of animals before, during and/or after exposure to the virus.

Acivicin inhibits IPNV replication both in vivo and in vitro. Acivicin is an analog of glutamine and a derivative of isoxasol. The effect of acivicin on IPN viral macromolecular synthesis, as described herein, shows that acivicin inhibits the formation of IPNV viral particles, even though it did not inhibit IPNV infected cells from synthesizing either viral polypeptides or genomic RNA. Furthermore, viral samples exposed to acivicin overnight had titers that were four orders of magnitude lower than the viral samples unexposed to acivicin; thereby indicating that acivicin effectively diminishes infective viral progeny. Additional preferred compounds for use in an embodiment of the present invention are compounds derived from isoxazol and denominated WIN compound.

The following test examples are intended to demonstrate the efficacy of the invention.

EXAMPLE 1

The Effect of Acivicin on Cell Viability

The effect of acivicin on cell viability is studied. No affect on the cells was observed using concentrations of acivicin that vary between 0 to 100 µg/ml. The $IC_{50}$ was obtained in concentrations ranging from 25 to 70 µg/ml, that is, 6 to 18 times higher than $EC_{50}$ and 3.5 to 7 times higher than $EC_{100}$. The effect of acivicin on RNA synthesis, protein synthesis and IPNV particle formation was examined.

Although acivicin is apparently a less effective inhibitor of IPNV replication as compared to reovirus, these concentrations of the compound do not affect the viability or the DNA synthesis of CHSE-214 cells. Acivicin has a good therapeutic index. Using similar assays to measure therapeutic index, isoxazol compounds are evaluated for their ability to inhibit the progression of IPNV infection in aquatic animals, particularly fish, thereby increasing the yield of fish and their total weight.

EXAMPLE 2

The Effect of Acivicin on IPNV Genomic RNA Synthesis

Figure 1:
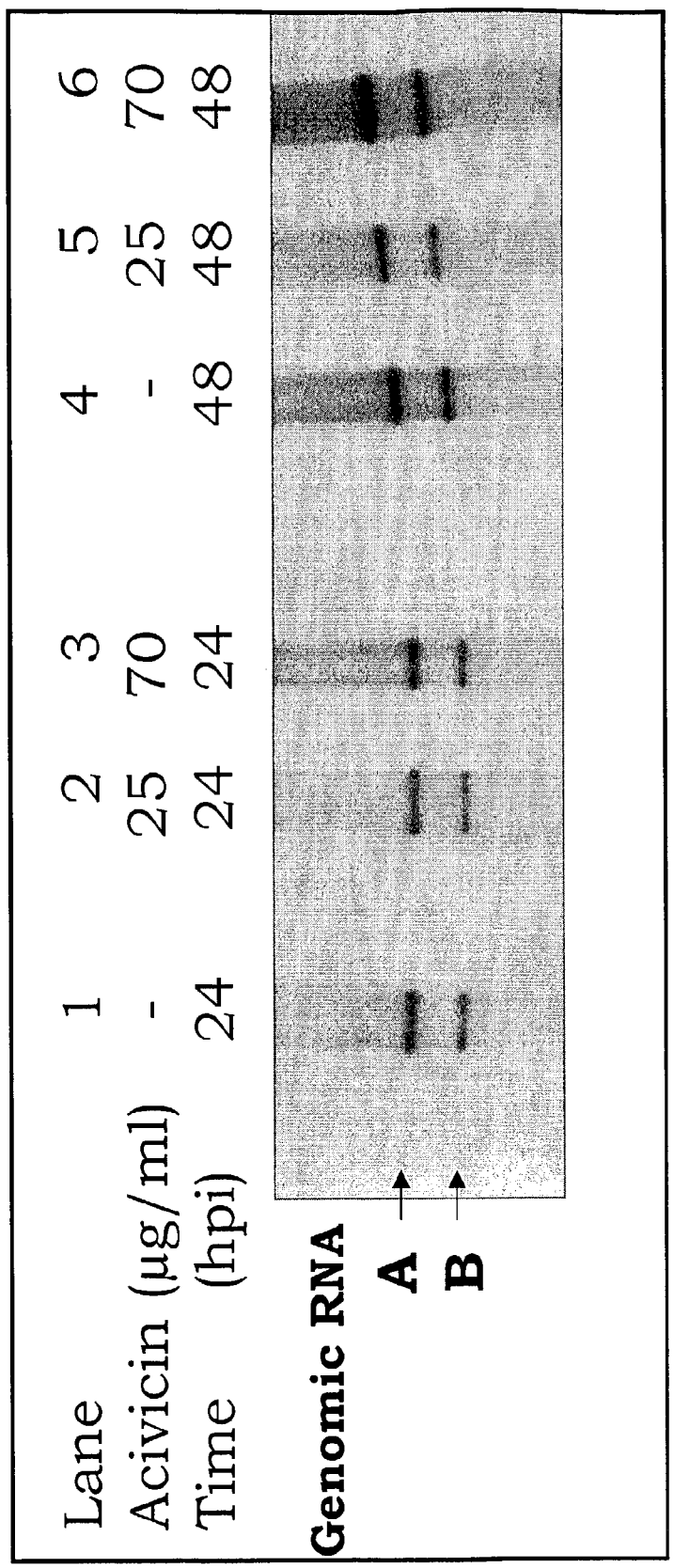
FIG. 1 is an autoradiograph showing the effect of acivicin on IPNV genomic RNA synthesis. Monolayers of CHSE-214 cells were infected with IPNV either in the absence (lanes 1 and 4) of acivicin, or the presence of acivicin at 25 µg/ml (lanes 2 and 5) or the presence of acivicin at 70 µg/ml (lanes 3 and 6). Simultaneously, acivicin and 50 µCi/ml of [$^{32}$P]-orthophosphoric acid were added at 0 hours post-infection (h.p.i.) and the cells were incubated at 15° C. At 24 hours post-infection (lanes 1, 2, and 3) and 48 hours post-infection (lanes 4, 5, and 6), the cells were harvested, RNA extracted therefrom, and analyzed by 7% polyacrylamide gel electrophoresis (PAGE) and autoradiography. The migration of the A and B segments of the IPNV genomic RNA is indicated by arrows.

The effect of acivicin on IPNV genomic RNA synthesis was determined, the results of which are shown in the autoradiograph of FIG. 1. Since IPNV genomic RNA can be detected from about 8 to 10 hours post infection, samples were evaluated at 24 hours and 48 hours post infection.

$6 \times 10^5$ CHSE-214 cells were infected at a m.o.i. of 50 pfu/cell. Monolayers of CHSE-214 cells were infected with IPNV either in the absence (lanes 1 and 4) of acivicin, or the presence of acivicin at 25 µg/ml (lanes 2 and 5) or the presence of acivicin at 70 µg/ml (lanes 3 and 6). Simultaneously, acivicin and 50 µCi/ml of [$^{32}$P]-orthophosphoric acid were added at 0 hours post-infection and the cells were incubated at 15° C. At 24 hours post-infection (lanes 1, 2, and 3) and 48 hours post-infection (lanes 4, 5, and 6), the cells were harvested, RNA extracted therefrom and analyzed by 7% polyacrylamide gel electrophoresis (PAGE) and autoradiography. The migration of the A and B segments of the IPNV genomic RNA is indicated by arrows.

EXAMPLE 3

The Effect of Acivicin on IPNV Polypeptide Synthesis

Figure 2:
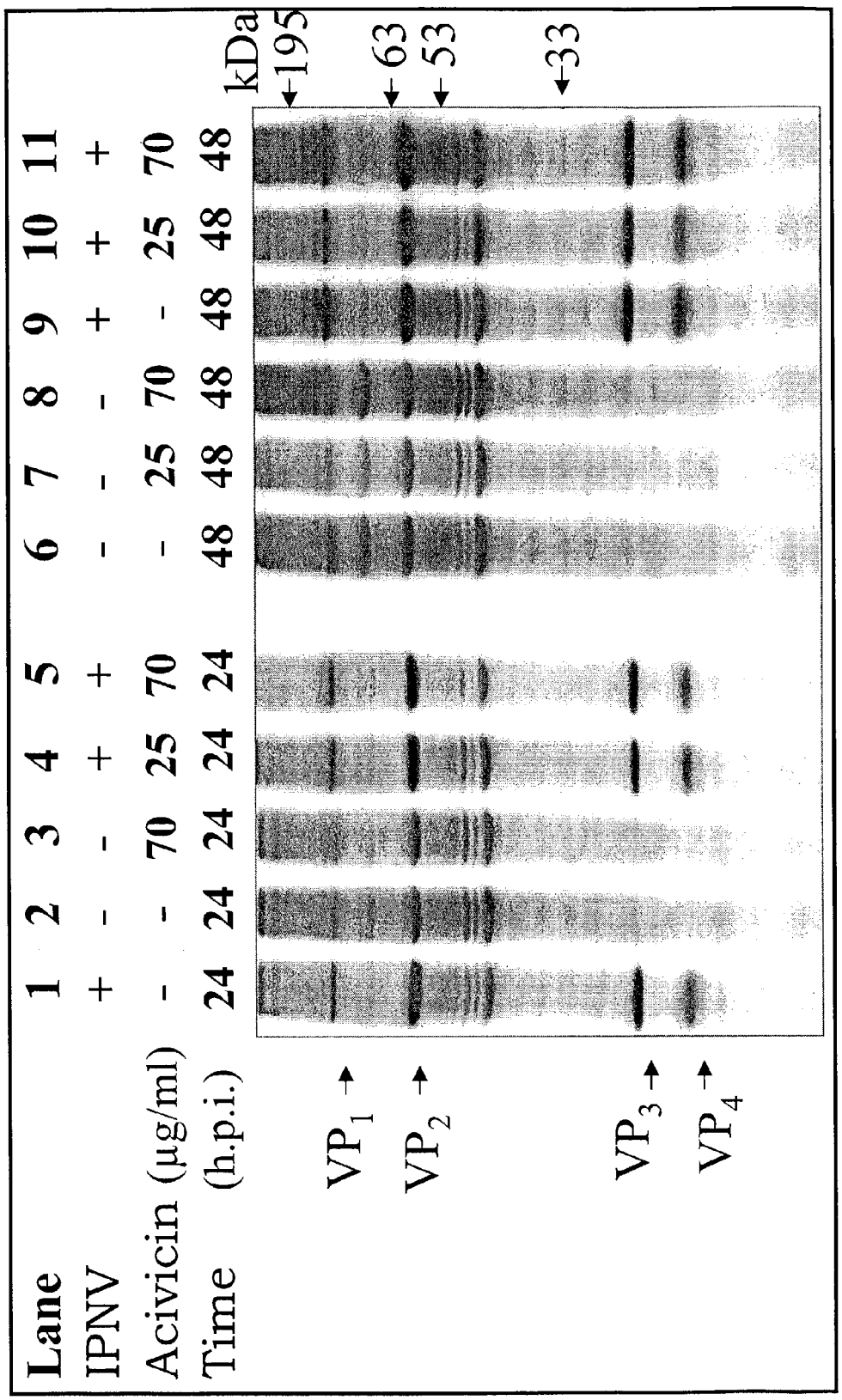
FIG. 2 is an autoradiograph showing the effect of acivicin on IPNV polypeptide synthesis. Monolayers of CHSE-214 cells were infected with IPNV either in the absence (lanes 1 and 9) or presence of acivicin at 25 µg/ml (lanes 4 and 10) or in the presence of acivicin at 70 µg/ml (lanes 5 and 11). Acivicin was added at the time of infection (zero h.p.i.) and the cells were incubated at 15° C. Six hours post-infection, a 50 µCi/ml of [$^{35}$S]-methionine was applied to the cells. At 24 h.p.i. (lanes 1 through 5) and at 48 h.p.i., 100 µl of a protein disruption solution was added to the cell monolayers. The polypeptides from the disrupted cells were analyzed by 15%

The effect of acivicin on IPNV polypeptide synthesis was determined, the results of which are shown in the autoradiograph of FIG. 2. Monolayers of CHSE-214 cells were infected with IPNV either in the absence (lanes 1 and 9) or presence of acivicin at 25 µg/ml (lanes 4 and 10) or in the presence of acivicin at 70 µg/ml (lanes 5 and 11). The acivicin was added at 0 h.p.i. and the cells were incubated at 15° C. Six hours post-infection, a 50 µCi/ml of [$^{35}$S]-methionine was applied to the cells. At 24 h.p.i. (lanes 1 through 5) and at 48 h.p.i. (lanes 6-11), 100 µl of a protein disruption solution was added to the cell monolayers. The polypeptides from the disrupted cells were analyzed by 15% SDS-PAGE and autoradiography. The controls of non-infected cells were also included in lane 2, 3, 6, 7, and 8. The migration of IPNV polypeptides is indicated.

EXAMPLE 4

The Effect of Acivicin on IPNV Particle Formation

The effect of acivicin on IPNV particle formation was determined, the results of which are shown in FIGS. 3A and 3B. To further characterize the effect of the isoxazol compound acivicin on the formation of IPNV particles, viral particles were evaluated in the absence and presence of acivicin. For this purpose monolayers of CHSE-214 cells in the presence of 25 and 70 µg/ml of acivicin, were infected for 24 and 48 hours and the particles were labeled both with $^{35}$S methionine and with $^{32}$P $H_2PO_3$. The particles were partially purified and visualized through electrophoresis in a tris-glycine agarose (TGA) gel. The $^{35}$S methionine labeled IPNV viral particle proteins were obtained in the absence of acivicin 24 or 48 hours post infection, as shown in FIG. 3A, lanes 3 and 6, respectively. Lanes 1, 2 and 4, 5 show the effect that the presence of 25 µg/ml and 70 µg/ml of acivicin, respectively, has on IPNV particle formation. The virus particles are obtained at 24 or 48 h.p.i., respectively. Similar results are obtain in the experimental method shown in FIG. 3B, in which the nucleic acid of the virus particles was labeled with $^{32}P$ $H_2PO_3$.

EXAMPLE 5

The Effect of Acivicin on Virus Cell Entry

Compounds derived from isoxazol are assayed for their ability to inhibit viral entry into the cell. To determine if acivicin blocks the entry of IPNV, a modified viral plaque inhibition assay was conducted. Prior to the viral inhibition assay, IPNV samples were pre-incubated overnight or for 2 hours with acivicin concentrations between 1 and 6 µg/ml. Control viral samples were not pre-incubated with acivicin. Results show that the samples pre-incubated overnight had an $EC_{50}$ of 2.5 µg/ml, which had diminished from 4 µg/ml, (which correspond to $EC_{50}$ of samples without pre-incubation). Overnight incubation of the virus in acivicin increased the ability of the isoxazol compound to inhibit viral plaques by 38 percent. The $EC_{50}$ of the viral samples that were pre-incubated for only 2 hours with acivicin were not significantly different from the viral samples that were not pre-incubated with acivicin.

To determine whether acivicin inhibits the assembly of infective viral progeny, the viral samples are titrated in the absence and presence of 4 µg/ml of acivicin. The methods are the same as the plaque reduction assay, except that the CHSE-214 cell monolayers were infected with serial dilutions of the virus from $10^{-1}$ to $10^{-9}$. Viral samples obtained from cells infected with virus in the absence of the compound had a titer corresponding to $3.7 \times 10^8$ pfu/ml while viral samples obtained from cells infected with virus in the presence of the compound had a titer corresponding to $4.3 \times 10^4$ pfu/ml. In other words, the titer of a viral sample diminished four orders of magnitude in the presence of acivicin. These results indicate that acivicin can effectively diminish the quantity and/or quality of infective viral progeny.

As shown in FIG. 3A, monolayers of CHSE-214 cells were infected with IPNV either in the absence (lanes 3 and 6) or in the presence of 25 µg/ml acivicin (lanes 1 and 4) or in the presence of 70 µg/ml acivicin (lanes 2 and 5). The acivicin antiviral compound was added at 0 h.p.i., the cells were incubated at 15° C. At 2 hours post-infection, 50 µCi/ml of [$^{35}S$]-methionine was applied to the cells. At 24 h.p.i. (lanes 1, 2 and 3) and 48 h.p.i. (lanes 4, 5, and 6), the particles were harvested, concentrated by ultracentrifugation and partially purified through a sucrose gradient. The viral particles were then subjected to electrophoresis in 0.8% Tris-glycine agarose gels and autoradiography. The migration of the IPNV particles are indicated.

FIG. 3B shows the results of experiments in which monolayers of CHSE-214 cells were infected with IPNV either in the absence (line 3 and 6) or in the presence of 25 µg/ml acivicin (lanes 1 and 4) or in the presence of 70 µg/ml acivicin (lanes 2 and 5), following the same procedures described for FIG. 3A, except that at 0 h.p.i., 50 µCi/ml of [$^{32}P$]-orthophosphoric acid were added.

EXAMPLE 6

The Effect of Acivicin on the Survival of IPNV-Infected Fry

Atlantic salmon fry (having an average body weight of about 1.0+/−0.2 g) are infected with $10^4$ pfu/ml IPNV by immersion on day 0. Starting nine days post-infection (day 9), surviving fish are divided into four groups of forty fish each and treated with 0, 7.0, 10.8, or 14.0 µg/ml of acivicin by immersion in a 2 hour daily bath containing 9 µg/ml of acivicin. One group corresponded to untreated fish, and the other three groups corresponded to fish groups treated with different concentrations of acivicin. As a negative control, there were two groups of 40 healthy fish in each; one group corresponded to an uninfected fry administered 14 µg/ml of acivicin while the other group was not infected or administered acivicin. Daily treatment in acivicin continued through day 21 post-infection (day 21). The fish were followed for 36 days post-infection to detect and document mortality. Results from days 10-24 are presented graphically in terms of "% survival" in FIG. 5.

The number of deaths among the Atlantic salmon fry infected with IPNV began on day 4 post-infection and increased progressively, reaching a 12% mortality rate on day 8 and 20% on day 9. Survival improved when treatment began on day 9 post-infection. In each of the treated groups, deaths began to diminish gradually, and stopped completely by day 10 post-treatment (day 19). After 12 days of acivicin treatment, the treatment was stopped (day 21 post-infection), which corresponded to when no further deaths were observed and the fish had resumed activity. Observations continued for 15 days further. Importantly, the IPNV-infected Atlantic salmon fry gradually stopped dying when the fry were treated with acivicin.

FIG. 5 shows the deaths that accumulated after acivicin treatment began on the 9th day post-infection (accumulated deaths presented as "% survival"). The accumulated deaths amongst the untreated fry infected with IPNV (positive control) reached 30% (i.e., 70% survival). In the group of infected fish treated with 7.0 µg/ml acivicin, the mortality rate also reached 30 percent. In the group of infected fish treated with 10.5 µg/ml acivicin, accumulated deaths reached 8%. In the group of infected fish treated with 14 µg/ml acivicin, mortality reached 11%. Five percent mortality was observed in the negative control group corresponding to uninfected fish. A three percent mortality rate was observed in the negative control group corresponding to uninfected fish treated with 14 µg/ml acivicin. The deaths among the uninfected fish were likely due to the handling of healthy fish during the experimental work, since no pathogen was found in fish tissue samples and the fish behavior was normal.

After the acivicin treatments were terminated, there were no deaths observed in any of the three groups that had been treated with the antiviral compound, nor in the uninfected control groups (days 21-36). In the infected untreated control group, however, deaths continued and reached 54 percent.

The groups treated with either 10.5 µg/ml or 14 µg/ml of the acivicin had survival rates that were the same as the uninfected controls, showing that acivicin is a strong inhibitor of IPNV morbidity and mortality in vivo. In addition, this antiviral compound is not toxic in fish, as evidenced by the uninfected fish treated with 14 µg/ml of acivicin, which had a survival rate equivalent to that of the uninfected and untreated fish. The higher survival was observed in the higher antiviral concentration, that is, 92% and 89% survival with 10.5 µg/ml and 14 µg/ml of acivicin, respectively.

It is important to not that there were progressive deaths in infected untreated fish as compared to the absence of further deaths in infected and treated fish after the acivicin treatments stopped. This indicates that the antiviral was effective in diminishing mortality during the acute period of the disease as well as after the antiviral was stopped. This is likely due to acivicin's ability to inhibit IPNV replication, which caused a marked decrease in the viral load so that the fry became asymptomatic carriers of the virus. This is corroborated by analyzing tissue samples from the fish in cell culture and RT-PCR assays described herein. In untreated infected fish, the viral titers can be over $10^5$ pfu/ml, while in treated fish viral titers are lower.

The presence of IPNV in the dead fish of both the treated and untreated groups was verified by the inoculation of monolayers of CHSE-214 cells and by the RT-PCR. These viral identification and quantification techniques were used because they are presently the most sensitive and reliable techniques available that allow for the detection of IPNV in fish carriers. At the end of the experiment, 45 days post-infection (day 45), samples were taken from the surviving fish to analyze whether they were carriers of the virus. The results of RT-PCR revealed the presence of the virus in all infected fish. However, a higher viral load was observed in untreated infected fish. A viral titer greater than $10^5$ pfu/ml was present in untreated fish while a viral titer between $10^2$ and $10^4$ pfu/ml was present in treated fish.

Aquatic birnavirus/IPNV can be classified and/or identified based on seroneutralization assays, cell culture assays, reverse transcriptase polymerase chain reaction (RT-PCR) assays, restriction enzyme analysis and/or sequence analysis. The RT-PCR assay is a rapid, specific and sensitive method to detect, identify and characterize aquatic birnaviruses that may be present in a sample. There are at least 9 type strains of Serogroup A and 4 other representative strains of Serotype A1 of IPNV, which is the predominant aquatic birnavirus and IPNV serotype in the United States. Primer sequences that are highly conserved among aquatic birnaviruses are used in PCR assays to identify all recognized serotypes of aquatic birnavirus serogroup A. Typical IPNV primers are specific for regions of cDNA coded by genome segment A or the entire VP2 coding region of aquatic birnaviruses.

When naturally infected rainbow trout fry of approximately 0.8 g were treated for 12 days with 9 μg/ml acivicin, the survival obtained was 98%, which suggests that an improvement in survival is obtained with concentrations that are greater than 7 μg/ml, such as about 9 μg/ml of this antiviral agent. With higher concentrations, survival was the same as that of healthy controls. This indicates that a plateau was reached in the antiviral effect of acivicin when using concentrations over 9 μg/ml.

The method of the present invention further includes administering an isoxazol compound before, during, and/or after IPNV exposure. In one embodiment, the method of the present invention commences administration of the isoxazol compound when mortality is observed to be from about 5% to about 25%, preferably on or before mortality reaches 20%.

EXAMPLE 7

In vitro Screening Compounds for Anti-Aquatic-Birnavirus Activity

The following compounds were screened for their ability to inhibit IPNV replication by the method described above:

- L (alpha S, 5S)-alpha-amino-3-chloro-4.5-dihydro-5-isoxazolacetic acid (acivicin); 6-(4-hydroxy-6-methoxy-7-methyl-3-oxo-5-phthalanyl)-4-methyl-4-hexenoic acid (mycophenolic acid);
- (S)-9-(2.3-dihydroxypropyl) adenine (DHPA);
- 3-adenine-9-yl-2-hydroxypropanoic acid (AHPA); and
- 3'-fluoro guanosine and 9-(2-hydroxy ethoxymethyl) guanine (acyclovir).

The antiviral effect of these compounds was evaluated by a virus plaque inhibition assay using procedures known in the art. Jashés et al, Antiviral Res. 29: 309 (1996). The assays were repeated at least three times and done in triplicate. Monolayers of Chinook salmon embryo cell line (CHSE-214) grown at 18° C. in a minimum essential Eagle medium (MEM), supplemented by 5% fetal bovine serum (FBS) and antibiotics to a confluence of about 90% are infected with about 50-100 plaque forming units (pfu) of IPNV strain VR-299. After one hour of absorption with agitation every 15 minutes, the sample was withdrawn and the cells were overlaid with 0.5% agarose in MEM supplemented with 10% FBS and incubated for 3 days at 15° C. The compounds being tested were added at different concentrations in the agarose overlay. Thereafter, the cells were formaldehyde-fixed and stained with a 0.5% crystal violet solution to detect lysis plaques. The compound concentrations used were selected on the basis of previous reports of other virus studies. The effective antiviral concentration required to inhibit IPNV plaque formation by 50% ($EC_{50}$) and by 100% ($EC_{100}$) was determined.

Table 3 shows the effects of several antiviral agents on IPNV replication in CHSE-14 cells.

TABLE 3

The Effect of Antiviral Agents on IPNV Replication in CHSE-14 Cells

| | Virus-plaque inhibition assay | | | Cytotoxic assays | |
|---|---|---|---|---|---|
| Antiviral compound | Concentration range assayed (μg/mL) | $EC_{50}$[a] (μg/mL) | $EC_{100}$[b] (μg/mL) | $CC_{50}$[c] (μg/mL) | $IC_{50}$[d] (μg/mL) |
| Ribavirin | 0.1-2.5 | 0.5 | 1 | N.A. | N.A. |
| Acivicin | 1-200 | 4 | 7 | >100 | 25-70 |
| Myconhenolic Acid | 0.05-20 | 0.5 | 1.5 | >50 | 1.8 |
| AHPA | 10-200 | 30 | N.D. | 75 | N.A. |
| DHPA | 1-200 | 50 | N.D. | 100 | NA |
| Acyclovir | 10-200 | N.I. | N.I. | N.A. | N.A. |
| 3'Fluoro Guanosine | 15-90 | N.I. | N.I. | N.A. | N.A. |

[a]Effective antiviral concentration required to inhibit IPNV plaque formation by 50%

[b]Effective antiviral concentration required to inhibit IPNV plaque formation by 100%.

[c]Cytotoxic concentration required to reduce cell viability by 50%.

[d]Inhibitory concentration required to reduce [methyl $^3$H] thymidine incorporation by 50%.

N.D. = Not determined, because at this concentration the compounds affect the cell monolayer avoiding the visualization of the plaques;

N.I. = Not inhibitory;

N.A. = Not analyzed.

Ribovarin was included as a reference compound; Table 3 shows results for ribovarin as those previously described. Hudson et al., Antiviral Res. 9: 379 (1988); Jashés et al, supra (1996).

Acyclovir, a guanosine analogue, though an inhibitor of viral polymerases did not inhibit IPNV replication in the concentration range studied (10-200 μg/ml). Similarly, 3'fluoro guanosine did not inhibit IPNV replication at higher concentrations than those described for other viruses by another 3'nucleoside analogues. Van Aersehot et al., Antiviral Res. 12:133 (1989).

The adenine analogues and the inhibitors of the enzyme S-adenosyl homocysteine hydrolase, DHPA and AHPA, inhibited IPNV plaque formation by 50%, with an $EC_{50}$ of 50 and 30 μg/ml respectively. When the antiviral concentrations were increased, the cell monolayers were affected so that plaque visualization was not possible and no $EC_{100}$ was obtained. DHPA had been described as an inhibitor of the IPNV replication in assays on RTG-2 cells at concentrations of 100 to 300 µg/ml, without presenting cytotoxicity. Nevertheless, CHSE-214 cells turned out to be more sensitive to this compound as well as to its AHPA analogue.

Of these compounds, only acivicin and mycophenolic acid at concentrations of 7 µg/ml and 15 µg/ml, respectively, were able to inhibit 100% ($EC_{100}$) the IPNV replication. Cytotoxicity studies were performed on acivicin and mycophenolic acid. The cytotoxic assay performed as described above determined concentrations required to reduce cell viability by 50% ($CC_{50}$) were higher than 100 µg and 50 µg respectively. The blockage of cellular DNA synthesis was measured for acivicin and mycophenolic acid. It was determined the concentrations that reduced the incorporation of [methyl $^3$H] thymidine by 50% ($IC_{50}$) were 25 to 70 µg/ml and 1.8 µg/ml, respectively. The difference between the inhibitory concentration of IPNV replication and the concentration that affects DNA synthesis in growing cells obtained with mycophenolic acid was not better than that previously described for other inosine monophosphate dehydrogenase inhibitors such as, ribavirin and EICAR. However, acivicin demonstrated a good therapeutic index.

Mycophenolic acid inhibited IPNV plaque formation in CHSE-214 cells, with an $EC_{50}$ of 0.5 µg/ml. This compound, like ribavirin and EICAR, acts by inhibiting the IMP dehydrogenase enzyme, thus decreasing the cellular GTP pool, which finally affects viral replication (Neyts et al., Antiviral Res. 30:125 (1996); Migus et al., J. Gen. Virol. 47: 47 (1980). In treating yellow fever virus, this compound was a more effective antiviral agent than either EICAR or ribavirin. Its $EC_{50}$ was ten times lower than that of EICAR and 350 times lower than that of ribavirin. Nonetheless, the antiviral effect of mycophenolic acid for IPNV was not greater than that for EICAR $EC_{50}$, which is 0.01 µg/ml. and it had the same $EC_{50}$ as ribavirin. Jashés et al., Antiviral Res. 29:309 (1996).

Acivicin inhibited IPNV plaque formation in CHSE-214 cells with a 4 µg/ml $EC_{50}$. The action mechanism of acivicin may be related to being a glutamine analog. Acivicin is an isoxazol derivative that is capable of acting in the same way that other such derivatives act to inhibit RNA virus replication in the virus family Picornaviridae by binding to the viral protein capsid. Such binding to the capsid prevents viral entry into the cell and denudation of the virus in the cell (Shepard et al., J. Virol. 67:2245 (1993). Acivicin inhibits reovirus replication in Balb/c cells at concentration at a concentration of 0.1 µg/ml. Keast et al., Arch. Virol. 124:235(1992). This concentration of acivicin is 40-times lower than that which inhibits IPNV replication in vitro. It is well known to those of skill in the art that the level of purity and activity of a compound may effect the required dose.

EXAMPLE 8

Assessing the Cytotoxicity of the Compounds

The cytotoxic effect on CHSE-214 of the compounds that inhibited the IPNV replication was studied using procedures previously described. The cytotoxic concentration required to reduce cell viability by 50% ($CC_{50}$) was determined. For example, adenine analogues AHPA and DHPA, the $CC_{50}$ obtained was 75 and 100 µg/ml, respectively and cytotoxicity was higher than that observed in RTG-2 cells. For mycophenolic acid, the $CC_{50}$ obtained was >50 µg/ml and the $IC_{50}$ of 1.8 µg/ml which was higher than the values obtained with ribavirin and EICAR for IPNV. Therefore, mycophenolic acid is not a better antiviral compound. See Neyts et al., Antiviral Res. 30:125 (1996). The cytotoxicity of these compounds in vivo can be lower that that measured by the $^3$H-thymidine uptake assays because the compounds may interfere directly with thymidine uptake. Drach et al., Science 212: 549 (1981).

EXAMPLE 9

The Effect of Acivicin on Naturally Infected Fish

Acivicin was tested in vivo on thirty rainbow trout (*Onchorhynchus mykiss*). Thirty naturally infected fry of rainbow trout (*Onchorhynchus mykiss*) weighing 1.0±0.4 g were treated for 15 days with 9 µg/ml acivicin, in a daily bath of two hours. The fish were followed for 30 days following the first day of the acivicin treatments. Deaths were documented and presented in terms of percent survival. Results from methods assessing the effect of acivicin treatment on the survival of the trout fry naturally infected are shown in the graph at FIG. 4. Thirty days after the acivicin administration began, 90% of the trout fry had survived , while only 30% of the untreated control group had survived the same 30 day period. The graph shows that in the treated fish group, the deaths all occurred by day 12 of the 15 day administration protocol; there were no further deaths observed after the $12^{th}$ day of the acivicin treatment. By contrast, in the untreated fish group, deaths continued during the first 25 days of the observation period.

EXAMPLE 10

Treatment of Salmon Fry with Acivicin Prior to Viral Infection

Atlantic salmon fry with are treated for a varying number of days (one day to 12 days) in a 2-hour daily bath with acivicin (concentrations varying between 7.0 and 25.0 ug/ml) prior to being experimentally infected with IPNV. Acivicin treatments continue after IPNV infection for 20 days or until there are no further deaths observed. Survival and viral titers are determined, as discussed above in EXAMPLE 5.

In an alternative protocol, the salmon are exposed to IPNV through exposure to IPNV infected fish. The Atlantic salmon fry uninfected with IPNV are divided into three groups of fish (Groups A-D) treated daily for 2 hours with the following four concentrations of acivicin: 7 µg/ml (Group A), 11 µg/ml (Group B), 15 µg/ml (Group C) and 0 µg/ml (Group D), respectively. On each successive day after day 1 of the acivicin treatment protocol, 30 fish from each group are exposed to 10 additional Atlantic salmon that are either (1) infected with IPNV (7 days post infection, having a viral titer averaging 20 pfu/ml) or (2) free of IPNV titers. Therefore, Groups A-1, B-1, and C-1 fish are acivicin-treated and IPNV-exposed; Group D-1 fish are untreated and IPNV-exposed; Groups A-2, B-2 and C-2 fish are acivicin-treated and not exposed to IPNV; and Group D-2 fish are not exposed to either acivicin or IPNV. Starting on day one of the acivicin treatment protocol, deaths are recorded and compared between the groups. The presence and titer of IPNV in the dead fish is determined by the inoculation of monolayers of CHSE-214 cells and by the RT-PCR.

EXAMPLE 11

The Time Course of Blood Isoxazol Concentration in Salmon

The active compound is mixed with minced horse mackerel and administered to in a single dose of 50 mg/kg by the free access method. At 6, 9, 12, 24, 36, 48 and 72 hours following administration, blood is taken from the heart. The concentration of the isoxazol compound in the blood is then determined by methods well known to those of skill in the art, such as by high pressure liquid chromatography (HPLC). The water temperature was measured daily during morning hours and recorded.

EXAMPLE 12

Preparation and Feeding Isoxazol Compounds to Fish

A powder is prepared by mixing 7 parts by weight of the isoxazol compound 2.0-5.0 g/kg with 93 parts by weight of lactose. Using 100 g of the powder as a daily dose unit, about 20,000 fish weighing 50 g on the average or a total of 1 ton are fed with a mixture of the above dose unit and 200 kg of minced fish for 5 consecutive days. This regimen is used to prevent and increase the survival of IPNV infection in the fish.

EXAMPLE 13

Preparation and Feeding Acivicin to Fish

A powder is prepared by mixing 7 parts by weight of acivicin with 93 parts by weight of lactose. About 15,000 fish weighing 200 g on the average or a total of 3 tons are given moist pellets, such as columnar pellets prepared by mixing minced sardine with a formulated feed power based on fish meal in a ratio of 6:4 and the mixture is formed into pellets mechanically) supplemented with 300 g of the acivicin powder for 5 consecutive days. This regimen is used to prevent and increase the survival of IPNV infection in fish.

Rainbow trout (*Onchorhynchus mykiss*) fry weighing 1±0.2 g that have been infected naturally are administered fish food with 0, 0.5, 1.0 and 2.0 mg acivicin/gram food daily for 15 days. The fish are monitored as described in Example 5 or Example 9, including for both survival and viral titers. The amount(s) or dose(s) at which survival improves significantly is then used as the effective amount administered in the fish food.

EXAMPLE 14

Treatment of Coho Salmon with Acivicin

Thirty Coho Salmon (*Onchorhynchus kisutch*) IPNV-infected fry weighing from about 0.7 to about 4.0 g are treated one day post infection for 7 days with 9 µg/ml acivicin, in a daily bath of one hour. The fish are followed for 22 days, to determine their mortality rate after treatment. The survival of the acivicin-treated fry and the untreated control group is compared.

EXAMPLE 15

Treatment of Rainbow Trout with Paramycin

Thirty rainbow trout (*Onchorhynchus mykiss*) fry weighing 1.0±0.2 g naturally infected with IPNV are treated for 15 days with 9 µg/ml paramomycin (available from Sigma), in a daily bath for two hours. The fish are followed for 4 weeks to determine their mortality rate after treatment. The survival of the paramomycin-treated fry and the untreated control group is compared.

EXAMPLE 16

Treatment of Rainbow Trout with Cycloserine

Thirty rainbow trout (*Onchorhynchus mykiss*) fry weighing 1.0±0.2 g naturally infected with IPNV are treated for 15 days with 9 µg/ml L-cycloserine (available from Sigma), in a daily bath of two hours. The fish are followed up for 15 more days. The survival of fry treated with L-cycloserine is documented and compared to determine the effectiveness and dose of the isoxazol compound that increases survival in the treated aquatic animals.

EXAMPLE 17

Treatment of Rainbow Trout with 4-bromohomoibotenic Acid

Thirty naturally infected rainbow trout (*Onchorhynchus mykiss*) fry weighing 1.0±0.2 g are treated for 15 days with 9 µg/ml (±)-4-Bromohomoibotenic acid (available from Sigma), in a daily bath of two hours. The fish are followed for 4 weeks to determine their mortality rate after treatment. The survival of the treated fry and the untreated control group is compared to determine the effectiveness and effective amount of the antiviral compound.

EXAMPLE 18

Treatment of *Salmo gairdneri* with isoxazole5-yl-2'-deoxyuridine:

Thirty naturally infected rainbow trout (*Salmo gairdneri*) fry weighing 1.0±0.2 g are treated for 15 days with 9 µg/ml 5-(isoxazol-5-yl)-2'-deoxyuridine, in a daily bath of two hours. The fish are followed for 4 weeks to determine their mortality rate after treatment. The survival of the treated fry and the untreated control group is compared to determine the effectiveness and effective amount of the antiviral compound..

EXAMPLE 19

Treatment of Oysters with Acivicin

Five hundred oysters (*Crassostrea virginica*) or shrimp naturally infected with a virus are treated for 30 days with 9 µg/ml acivicin, in a daily bath of six hours. The mollusk is followed up for 1 year, to detect a possible outbreak of mortality after treatment. The final survival of acivicin treated oysters and untreated oysters are observed. . The final survival of acivicin treated shrimp and untreated shrimp are observed and compared to determine the effectiveness and effective amount of the antiviral compound.

EXAMPLE 20

Administration of Isoxazol in Fish Farming

A fish farm raising King Salmon (*Onchorhynchus tshawytscha*) monitors fry activity and appearance, looking for fry that appear dark, located up against water outflows, and/or "shivering" near the surface. Shivering fish are caught and are examined for the white mucus in the stomach characteristic of IPNV infection. Upon detection of such fish, all fry are treated for 15 days with 9 µg/ml acivicin, in a daily bath of two hours. After the treatment, the fish are closely monitored for an additional 2-3 weeks, to determine their mortality rate after treatment. The survival of the treated fry and the untreated control group is compared to determine the effectiveness and effective amount of the antiviral compound.

EXAMPLE 21

The Effect of Neomycin on IPNV RNA Synthesis

The effect of neomycin on IPNV genomic RNA synthesis was determined. the results of which are shown in the autoradiograph of FIG. 6A. Monolayers of Chinook salmon embryo cell line 214 (CHSE-214) cells were infected with IPNV either in the absence (lanes 3,5,7 and 9) of neomycin, or in the presence of neomycin at 4 mg/ml (lanes 2, 4, 6 and 8). Neomycin was added to the cells at 1, 3, 5 and 7 hours post-infection (h.p.i.), (lanes 2, 4, 6 and 8) respectively, and the cells were incubated at 15° C. At 24 hours post-infection the cells were harvested, RNA extracted therefrom, and analyzed by 7% polyacrylamide gel electrophoresis (PAGE) stained with silver nitrate. Lane 1 shows a control of IPNV genomic RNA. The data show that Neomycin inhibited the IPNV RNA synthesis.

EXAMPLE 22

The Effect of Acivicin on IPNV Polypeptide Synthesis

The effect of neomycin on IPNV polypeptide synthesis was determined, the results of which are shown in the autoradiograph of FIG. 6B. Monolayers of CHSE-214 cells were infected with IPNV either in the absence (lanes 3,5,7 and 9) or presence of neomycin at 4 mg/ml (lanes 2, 4, 6 and 8). Neomycin was added at 7, 5, 3 and 1 hour post-infection (h.p.i.), (lanes 2, 4, 6 and 8) respectively, and the cells were incubated at 15° C. At four hours post-infection, 50 µCi/ml of [$^{35}$S]-methionine was applied to the cells. At 24 h.p.i. 100 µl of a protein disruption solution was added to the cell monolayers. The polypeptides from the disrupted cells were analyzed by 15% SDS-PAGE and autoradiography. Lane 1 is a control of uninfected CHSE-214 cells. Neomycin does not inhibit IPNV polypeptide synthesis.

EXAMPLE 23

The Effect of Neomycin Treatment on the Survival of IPNV-Infected Fry

Atlantic Salmon fry (having an average body weight of about 0.75+/-0.3 gm) are infected with $10^4$ pfu/ml IPNV on day 0. One day post-infection, the fish are treated daily by immersion for 1 hour in a bath containing 10, 40 or 80 ppm of neomycin. Control uninfected fish fry are either treated daily for one hour with 0 or 80 ppm of neomycin. This daily treatment in neomycin continued through day 10 post-infection. The fish were followed for 26 days post-infection to document deaths. The results are presented graphically in terms of "% survival" in FIG. 7. Treatment of IPNV infected salmon fry at concentrations as low as 10 ppm can maintain survival to levels equivalent to the uninfected controls.

EXAMPLE 24

The Survival of IPNV-Infected Fry Treated with Neomycin Nearly Two Weeks Post-Infection Salmon fry weighing about 0.45 to about 1.0 gms were infected on day 0 with $10^5$ pfu/ml of IPNV. Starting thirteen days post-infection, after the mortality outbreak began, the fish are treated daily by immersion for 1 hour in a bath containing 10, 40 and 80 ppm of neomycin, and continued through day 23 post-infection. The fish were followed for 26 days post-infection to document deaths. Results are presented graphically in FIG. 8 in terms of percent survival. Importantly, the IPNV-infected Salmon fry stopped dying immediately when the fry were treated with neomycin.

The foregoing disclosure of the preferred embodiments of the present invention has been presented for purposes of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

Further, in describing representative embodiments of the present invention, the specification has presented the method as a series of steps. However, to the extent that the method does not rely on the particular order o steps set forth herein, the method should not be limited to the particular sequence of steps described. As one of ordinary skill in the art can appreciate, other sequences of steps may be possible. Therefore, the particular order of the steps set forth in the specification should not be construed as limitations on the claims. In addition, the claims directed to the method of the present invention should not be limited to the performance of their steps in the order written and one skilled in the art can readily appreciate that the sequences may be varied and still remain within the spirit and scope of the present invention.

What is claimed is:

1. A method of treating a fish infected with infectious pancreatic necrosis virus (IPNV) comprising feeding fish food containing 1 μg to 100 μg of acivicin per gram of food to the fish.

2. A method of increasing the survival of a fish infected with infectious pancreatic necrosis virus (IPNV), comprising administering an effective amount of acivicin to the fish wherein the effective amount is a concentration from about 7.0 μg/ml to about 30 μg/ml of water in the fish's environment.

3. The method of claim 2, wherein said administering is by a method selected from the group consisting of: introducing the compound into the aquatic environment; including the compound in food; and injecting into the fish the compound dissolved in a pharmaceutically acceptable carrier.

4. The method of claim 2, wherein the effective amount is a concentration that is capable of increasing the fish's likelihood of survival by from about 10% to about 70%.

5. The method of claim 2, wherein the effective amount is a concentration that increases the fish's likelihood of survival by from about 10% to about 30%.

6. The method of claim 2, wherein the effective amount is a concentration that inhibits viral replication in the fish.

7. The method of claim 2, wherein the effective amount is a concentration that decreases the quantity of the IPNV in a tissue of the fish.

8. The method of claim 2, wherein the effective amount is a concentration that decreases the quantity of IPNV in a tissue of the fish from about 105 pfu/ml to a viral titer of from about 101 to about 103 pfu/ml.

9. The method of claim 2, wherein the effective amount is a concentration that decreases the viral load/viral titer of the IPNV in a tissue of the fish by from about 101-fold to about 104-fold.

10. The method of claim 2, wherein the effective amount is a concentration that decreases the viral titer of the IPNV in a tissue of the fish by from about 10-fold to about 100-fold.

11. The method of claim 2, wherein the effective amount is a concentration from about 9.0 μg/ml to about 14.0 μg/ml of water in the fish's environment.

12. The method of claim 2, wherein the fish is selected from the group consisting of fish from the families Anguillidae, Bothidae, Caragidae, Cotostomidae, Chichlidae, Clupeidae, Cobitidae, Coregonidae, Cyprinidae, Esocidae, Moronidae, Paraichthydae, Percidae, Poecilidae, Salmonidae, Salvelinus, Sciaenidae, Thymallidae and the species *Seriola quinqueradiata* (yellowtail), *Scopthalmus maximus* (turbot), *Limanda limanda* (dab), *Hippoglossus hippoglossus* (halibut), *Gadus morhua* (Atlantic Cod), *Misgrunus anguillisaudatus* (loach), and *Esox lucious* (pike).

13. The method of claim 2, wherein fish is in the Salmonidae or Salvelinus family and selected from the group consisting of trout, *Oncorhynchus tshawytscha* (Chinook, King, or Spring), *Oncorhynchus nerka* (Blueback, Red, Sockeye), *Oncorhynchus kisutch* (Coho, Silver), *Oncorhynchus gorbuscha* (Pink), *Onchorhynchus mykiss* (Rainbow trout), *Oncorhynchus keta* (Chum, or Keta), *Oncorhynchus mason* (Masou, or Cherry), and *Salmo salar* (Atlantic salmon).

14. The method of claim 1, wherein said fish food is a moist pellet.

15. The method of claim 2, wherein the effective amount slows or stops the progression of infectious pancreatic necrosis disease in the fish.

16. The method of claim 2, wherein the fish is selected from the group consisting of: salmon, rainbow trout, and brook trout.

17. The method of claim 2, wherein the fish weighs from about 0.6 grams to about 10 grams.

18. The method of claim 2, wherein the fish weighs from about 10 grams to about 200 grams.

19. The method of claim 2, wherein the fish weighs from about 200 grams to about 5000 grams.

20. The method of claim 2, wherein said administering occurs after the clinical signs of IPNV are detected in said fish and/or after the detection of IPNV in a tissue from the fish.

21. The method of claim 1, wherein said concentration is from about 5 μg to about 25 μg per gram of food.

22. The method of claim 2, wherein the effective amount slows or stops the progression of IPNV disease in the fish.

23. A method of increasing survival in a population or group of fish infected with IPNV, comprising administering an effective amount of acivicin to the population or group of fish wherein said administering occurs after the detection of a mortality outbreak and/or decreased survival among the population or group of fish wherein the effective amount is a concentration from about 7.0 μg/ml to about 30 μg/ml of water in the fish's environment.

* * * * *

UNITED STATES PATENT AND TRADEMARK OFFICE
CERTIFICATE OF CORRECTION

PATENT NO.      : 7,652,050 B2
APPLICATION NO. : 10/314366
DATED           : January 26, 2010
INVENTOR(S)     : Sandino et al.

It is certified that error appears in the above-identified patent and that said Letters Patent is hereby corrected as shown below:

Title page, Item (73) Assignee: "Laboratorio de Siagnóstico GAM S.A" should read --Laboratorio de Diagnóstico GAM S.A--

Signed and Sealed this
Twenty-eighth Day of December, 2010

David J. Kappos
*Director of the United States Patent and Trademark Office*